US010485689B1

(12) United States Patent
Walsh et al.

(10) Patent No.: US 10,485,689 B1
(45) Date of Patent: *Nov. 26, 2019

(54) VRB CANTILEVER-BASED UNLOADER BRACE ASSEMBLY

(71) Applicant: Alliance Design and Development Group, Inc., Matawan, NJ (US)

(72) Inventors: Robert Walsh, Matawan, NJ (US); Peter B. Tarlton, Reading (GB)

(73) Assignee: Alliance Design and Development Group, Inc., Matawan, NJ (US)

(*) Notice: Subject to any disclaimer, the term of this patent is extended or adjusted under 35 U.S.C. 154(b) by 311 days.

This patent is subject to a terminal disclaimer.

(21) Appl. No.: 15/438,367

(22) Filed: Feb. 21, 2017

Related U.S. Application Data

(63) Continuation of application No. 14/490,416, filed on Sep. 18, 2014, now Pat. No. 9,610,188, and a continuation-in-part of application No. 13/622,331, filed on Sep. 18, 2012, now abandoned.

(60) Provisional application No. 61/880,147, filed on Sep. 19, 2013, provisional application No. 61/986,077, filed on Apr. 29, 2014, provisional application No. 61/585,315, filed on Jan. 11, 2012.

(51) Int. Cl.
| | | |
|---|---|---|
| A61F 5/01 | (2006.01) |
| A61H 3/00 | (2006.01) |
| A63B 49/02 | (2015.01) |
| A63B 53/10 | (2015.01) |
| A63B 59/20 | (2015.01) |
| A63B 59/50 | (2015.01) |
| A63B 71/06 | (2006.01) |

(52) U.S. Cl.
CPC .......... *A61F 5/0125* (2013.01); *A61H 3/00* (2013.01); *A63B 49/02* (2013.01); *A63B 53/10* (2013.01); *A63B 59/20* (2015.10); *A63B 59/50* (2015.10); *A61F 2005/0139* (2013.01); *A63B 2071/0694* (2013.01)

(58) Field of Classification Search
CPC .... A61F 5/0123; A61F 5/0125; A61F 5/0106; A61F 2005/0139; A61F 5/0109; A61F 5/0111; A61F 5/0585; A61F 5/0127; A61F 13/061; A61F 2005/0167; A61F 2005/0146; A61F 2005/0144; A61F 2005/0153; A61F 2/64
See application file for complete search history.

(56) References Cited

U.S. PATENT DOCUMENTS 9,610,188 B2 * 4/2017 Walsh ................ A61F 5/0123

* cited by examiner

*Primary Examiner* — Ophelia A Hawthorne
(74) *Attorney, Agent, or Firm* — Law Office of Carl Giordano, PC

(57) ABSTRACT

An Unloader assembly to control load distribution about a joint is disclosed. The assembly including an upper collar attachable above the joint and a lower collar attached below the joint, and a hinge positioned between the upper attachment and the lower attachment. The Unloader further includes a compression assembly includes an arm attached at one end to the hinge and a housing into which the arm is slidable. The housing further includes a bushing and a variable resistance beam positioned between the arm and the bushing. The variable resistance beam provides a variable degree of rigidity to provide different levels of resistance to compression.

11 Claims, 39 Drawing Sheets

(a)

Type I

Fulcrum Resistance = Hand Positions = A, B, C, D, E, Indicia (b)

(c)

VRB CANTILEVER-BASED UNLOADER BRACE ASSEMBLY

CLAIM OF PRIORITY

This application claims,
pursuant to 35 USC 120, as a Continuation application, priority to and the benefit of, the earlier filing date of that patent application entitled:
VRB Cantilever Based Unloader Brace Assembly, filed on Sep. 18, 2014 and afforded Ser. No. 14/490,416 (now U.S. Pat. No. 9,610,188) which claimed:
pursuant to 35 USC 119, priority to and the benefit of the earlier filing date of that patent application entitled:
"Exo-Unloader Knee Brace," filed on Sep. 19, 2013 and afforded Ser. No. 61/880,147; and
pursuant to 35 USC 119, priority to and the benefit of the earlier filing date of that patent application entitled:
"Methods for Adjusting Stiffness and Flexibility in Medical Braces, Devices, Apparatus and Equipment," filed on Apr. 29, 2014 and afforded Ser. No. 61/986,007; and
pursuant to 35 USC 120, as a continuation-in-part, priority to and the benefit of the earlier filing date of that patent application entitled:
"Methods for Adjusting Stiffness and Flexibility in Devices, Apparatus and Equipment," filed on Sep. 18, 2012 and afforded Ser. No. 13/622,331, now abandoned, which claimed,
pursuant to 35 USC 119, priority to and the benefit of the earlier filing date of than patent application entitled:
"Exercise Apparatus Having a Resilient Solid Beam with Geometric Protrusions on the Outside for Adjusting Resistance and Stiffness," filed on Jan. 11, 2012 and afforded Ser. No. 61/585,315, the contents of all of which are incorporated, in their entirety, by reference herein.

FIELD OF THE INVENTION

The invention relates the field of equipment and more particularly to devices, apparatus and equipment whose degree of stiffness and flexibility may be varied or dynamically controlled. Particularly, this application relates to the field of an exoskeleton device and more particularly to an exoskeleton unloader brace assembly.

BACKGROUND

There is a need for varying and adjusting the flexibility and stiffness of associated devices, apparatus and equipment to customize to a user's unique needs, and to the requirements of a particular task or desired outcome.

For example, in recent years, as it relates to the category of sports and fitness equipment, manufacturers and marketers have increasingly turned to different kinds of methods to enhance the customization and performance of sporting and fitness equipment. In some cases, entire lines of sporting equipment have been developed whose stiffness or flexibility characteristics are different from each other and are designed to be matched to the user's unique needs. Such differences, however, may be enough to give the individual equipment user an edge over the competition in that the equipment can be more personally customized, matched to a desired goal, and, therefore, enhance performance.

Until now, the user may choose a particular piece of sporting or fitness equipment having a desired stiffness or flexibility characteristic and, during play, switch to a different piece of sporting equipment that is slightly more flexible or stiffer to suit changing playing conditions or to help compensate for weariness or fatigue or some other anomaly that prevents optimum performance. Such switching, of course, is subject to the availability of different pieces of sporting or fitness equipment from which to choose, at the precise moment the change or adjustment is needed. In many cases, the availability is limited due to cost and over all impracticability.

Additionally, subtle but important changes in the stiffness or flexibility characteristics of sporting or fitness equipment may not be available between different pieces of sporting equipment, because the characteristics may be set by the manufacturer from the choice of materials, design, etc., and to change the characteristics would be impossible, as such customization isn't offered to the user. Further, the user must have the different pieces of sporting equipment nearby during play or they are essentially in practice unavailable to the user.

Thus, it can be seen how the lack of adjustability in stiffness and flexibility may adversely affect optimum performance of a device, apparatus, and equipment.

Turning to additional types of devices, apparatus and equipment, it can be seen how the lack of a practical means of adjustability in stiffness and flexibility may adversely affect performance.

Medical Devices, Apparatus, and Equipment

Medical devices, apparatus and equipment, such as braces that are used for supporting injured limbs, require the flexibility of the device to be adjusted based on the degree of the injury, type of surgery, and the progress of the healing of the injured party. Further, there is a need for on-going protection even after recovery. Yet the degree of adjustability of braces is limited, and, in most cases, fixed. Adjustability of the flexibility of the brace the brace to the specific needs and requirements of the user, may enhance recovery and protection from further injury.

Medical braces are commonly used to support joints, e.g., elbows, knees, ankles, etc., either to protect the joint during strenuous activities or to provide support when the joint has been injured and is healing. Sports braces are commonly used to support joints when participating in athletic activities.

One type of brace is a simple bandage that wraps around the joint, applying a compression force around the joint. Another type of brace is an exoskeleton that locks the joint in a particular configuration.

The exoskeleton type knee brace, which is typically attached between a thigh and a calf, is commonly used to support the body's weight and maintain the intervening knee in a fixed plane of articulation, with the principle axial bend registered below the medial and lateral condyle of the femur. The brace distributes the user's weight around the knee so that the intervening knee is relieved of the pressure that is placed on it by the user's weight. By removing the pressure of the user's weight from the knee, further damage to the knee is avoided and a damaged knee recovers.

Fitness Devices, Apparatus, and Equipment

Fitness equipment, apparatus and devices require the creation of different amounts of resistance to perform the exercise. For example, with free-weight training the user must change the weight levels to progressively increase the resistance that the user experiences. This often involves the continued and time consuming adjustment of equipment through an exercise cycle and makes changes impractical at best, and at the least a hassle.

Numerous heavy metal plates, large oily machines, weights, rubber bands, and singular resistance rods are the many known forms of fitness training. When the user changes resistance/weight or machine during an exercise set, it is time consuming and interrupts the user's conditioning.

Running Shoes, Training Shoes, Basketball Shoes

The transmission of the shoe wearer's strength (power) from their legs into the ground is directly affected by the sole stiffness of the shoe. Runners may gain more leverage and, thus, more speed by using a stiffer sole. Basketball players may also affect the height of their jumps through the leverage transmitted by the sole of their shoes. If the sole is too stiff, however, the toe-heel flex of the foot is hindered. Thus, athletic shoes are tailored, by the manufacturer, to the particular sport to which the shoe is to be used. In some case, it may be possible for the user have the ability to tailor the sole stiffness to his/her individual weight, strength, height, running style, and ground conditions. However, this process is performed by the manufacturer and is beyond the ability of the average user.

Golf

Golf clubs may be formed of graphite, wood, titanium, glass fiber or various types of composites or metal alloys. Each material varies to some degree with respect to stiffness and flexibility. However, golfers generally carry onto the golf course only a predetermined number of golf clubs. Varying the stiffness or flexibility of the golf club is not possible, unless the golfer brings another set of clubs. Nevertheless, it is impractical to carry a large number of golf clubs onto the course, wherein each club having a slight nuance of difference in flexibility and stiffness than another. Golf players prefer taking onto the course a set of clubs that are suited to the player's specific swing type, strength and ability.

Hockey

Hockey (hockey includes, but is not limited to, ice hockey, street hockey, roller hockey, held hockey and floor hockey) players may require that the flexure of the hockey stick be changed to better assist in the wrist shot or slap shot needed at that particular junction of a game or which the player was better at making.

Younger players may require more flex in the hockey stick due to lack of strength; such flex may mean the difference between the younger player being able to lift the puck or not when making a shot since a stiffer flex in the stick may not allow the player to achieve such lift. In addition, as the younger players ages and increases in strength, the player may desire a stiffer hockey stick, which in accordance with conventional means the hockey player would need to purchase additional hockey stick shafts with the desired stiffness and flexibility characteristics. Indeed, to cover a full range of nuances of differing stiffness and flexibility characteristics, hockey players would have available many different types of hockey sticks. Even so, the hockey player may merely want to make a slight adjustment to the stiffness or flexibility of a hockey stick to improve the nuances of the play; which is not possible with conventional technology Tennis Tennis players also may want some stiffness and/or adjustability in their tennis rackets and to resist unwanted torsional effects caused by the ball striking the strings during play. The torsional effects may be more pronounced in the case where the ball strikes near the rim of the racket rather than the center of the strings.

Lacrosse

Lacrosse players use their lacrosse sticks to scoop up a lacrosse ball and pass the ball to other players or toward the goal. The stiffness or flexibility of the lacrosse stick may affect performance during the game.

Other Racket Sports

Other types of racket sports also suffer from the drawback of being unable to vary the stiffness and/or flexibility of the racket during the course of play to suit the needs of the player at that time, whether those needs arise from weariness, desired held positions, or training for improvement. Such racket sports include racquetball, paddleball, squash, badminton, and court tennis.

For conventional rackets, the stiffness and flexibility is set by the manufacturer and invariable. If the player tires of such characteristics being fixed or otherwise wants to vary the stiffness and flexibility, the only practical recourse is to switch to a different racket whose stiffness and flexibility characteristics better suit the needs of the player at that time.

Skiing, Snowboarding, Snow Skating, Ski-boarding

Skis are made from a multitude of different types of materials and dimensions, the strength and flexibility of each type differing to a certain extent. Skis include those for downhill, ice skiing, cross-country skiing and water-skiing. For soft snow conditions, the rider may want to have more flexibility so as to allow the board to float. For icier conditions, the rider may want to stiffen the highback to provide greater leverage and power, which results in greater edge control.

Bicycle Shoes

Bicycle specific shoes are rigid and may or may not be attached to bicycle pedals usually through a binding or clip mechanism that prohibits the shoe from slipping of the pedal. The shoe is positioned on the pedal so the ball of the foot is directly over the pedal. The rider's foot flexes as the pedal moves. However, the bicycle shoe is designed for pedaling and walking in these shoes is uncomfortable.

Fishing Rods

Fishing rods are flexed for casting out a line. The whip effect from the casting is affected by the stiffness or flexibility of the rod. Depending upon the fishing conditions and the individual tastes of the user, the user may prefer the rod to be either more flexible or stiffer to optimize the whip effect of the cast and to deal with wind, current, types of fish, and the like. Thus, the user must select the type of flexibility or stiffness when purchasing the fishing rod.

Fins

Diving and swimming fins provide different degrees of stiffness that are fixed, and unchangeable. However, the need to have more flex or less flex and, thus, control fin bend is dependent on the changing conditions. Optimum performance that matches the conditions may be possible with dynamically adjustable fin spine(s). It would also be advantages in that the swimmer/diver would not be unnecessarily fatigued if they had proper matching flex to the conditions.

Sailboating and Sailboarding

Masts of sailboats and sailboards support sails. In many cases the users must adjust the amount of sail that is hanging from the mast according to the weather conditions to prevent damaging the mast caused by stress on the mast.

Canoeing, Rowboating and Kayaking

Paddles for canoes, row boats, and kayaks are subjected to forces as they are stroked through water. The flexibility or stiffness of the paddles, while different depending upon its design and materials, is fixed by the manufacturer. Thus, a rower who desired to change such characteristics would need to switch to a different type of paddle. Carrying a multitude of different types of paddles for use with a canoe, rowboat or kayak, however, is generally impractical for the typical rower from the standpoint of cost, bulk and storage.

Lawn Rake

There are times when the flex of a rake's tines are either too flexible or too stiff for the task at hand, be it for raking gardens, light leaf, matted thatch, wet grass, debris. Often the user has to purchase a second rake to accommodate these additional needs.

Hence, there is a need in a plurality of industries in which adjustment of the flexibility or stiffness of a device, apparatus or equipment would be advantageous. Particularly, there is a need for an exoskeleton type brace that allows for additional flexibility in the brace and also the amount of pressure that is relieved from the knee.

SUMMARY OF THE INVENTION

The invention relates to a variable resistance beam or rod that may dynamically control the stiffness and flexibility of devices, apparatus, and equipment. The resilient rods, beams or shafts of solid, semi-solid or hollow construction produce resistance and variable resistances when orientated in a direction of x, y, z plane or combination of planes in 360 degrees of rotation or bending movement.

The variable resistance rod (VRB) technology may be incorporated into different equipment (sports & fitness, lawn, medical, etc.) that require different degrees and direction of stiffness and flexibility, wherein the different degrees of stiffness and flexibility may be controlled in the field in real time by means of a selector, a worm gear, or other mechanical methods to affect a rotated orientation of the variable resistance rods, or by simple hand placement in relation to the fulcrum indicated by an indicia of color, number, symbol or other means.

One aspect of the invention resides in a resilient or resistance rod acting to create variable resistance that incorporates a selectable or adjustable flex resistance by means of hand position and placement.

One aspect of the invention resides in a resilient rod, beam or shaft, including at least one spine, extending substantially the length of the rod, beam or shaft, that provides for variable degrees of flexibility of the rod, shaft or beam depending upon the orientation of the spine with regard to a direction of flex.

One aspect of the invention resides in equipment that adjusts to provide variations in stiffness and flexibility. The equipment may have a rod, beam or shaft with an elongated cavity or rod, an elongated flexure resistance spine, one, two or more locking elements that secure the rod, shaft or beam against rotation at spaced apart locations within the cavity. The rod, shaft or beam is stiffer and less flexible in one direction than in another.

Another aspect of the invention resides in sports equipment that provides variations in stiffness and flexibility. The sports equipment may have an elongated cavity, and a means imparting stiffness and flexibility variations within the cavity so the sports equipment becomes stiffer, and less flexible, in one direction than in another, and one or more locking elements that secure the means against rotation in spaced apart locations within the cavity.

A further aspect of the invention resides in a method of varying stiffness and flexibility, comprising providing equipment (e.g., sports & fitness, medical, footwear & sneakers) having an elongated cavity; imparting stiffness and flexibility variations within the cavity so that the equipment becomes stiffer and less flexible, in one direction than in a different direction; and securing against rotation at least one location within the cavity while imparting stiffness and flexibility variations.

An additional aspect of the invention resides in a resilient shaft or beam acting alone to create variable resistance that incorporates a selectable or adjustable flex resistance by means of varying hand position and placement on the resilient rod in relationship to the fulcrum of the bended rod.

An advantage of the present invention is the ability to provide constant and consistent flex adjustment. This advantage arises from the adjustment being locked in at the ends of the shaft and, depending upon the application, at one or more additional locations through the length of the shaft.

A resilient rod acting alone is also embodied to create resistance that incorporates adjustable flex or resistance by means of hand position and/or specific rotation for means of exercise employing progressive dynamic resistance, which relates to the advantages in exercise of varying degree weight and resistance through a particular cycle.

The present invention provides an exoskeletal technology that delivers a medically prescriptive knee brace, which provides a mission adaptable brace by selecting a supportive range to protect the joints of the body (e.g., a knee) by unloading pack-weights so as to increase mobility and provide for support during activities (recuperation, athletic, etc.).

The present invention provides an unloader assembly to control load distribution about a joint by providing selectable levels of protection for all sports, extreme sports, military missions, prophylactic protection, rehabilitation and osteoarthritic applications.

In one embodiment of a exoskeletal structure suitable for supporting a knee joint, a knee brace configuration is disclosed that selectively unloads body weight from the (patella-femoral) knee joint using a VRB (Variable Resistant Beam) as a cantilever.

The VRB selective resistance cantilever provides a prescriptive range of lift to support and unload body weight from the knee joint.

The lift created by the locked VRB rotated selection gently separates and dynamically suspends the knee joint in proportion to loading.

The VRB cantilever additionally acts as a dynamic leaf spring to provide incremental reactive suspension to cushion the knee joint.

The VRB selectively and incrementally thereby prescriptively unloads or lifts body weight from the knee joint proportional to its resistance or fixed rotation.

The VRB incrementally and selectively unloads, lifts or separates the knee joint or the bones of the knee joint in the order of 1 mm (millimeter) to 3 mm and up to a maximum of 5 mm to provide pain relief for OsteoArthritic, Post Injury/Operative patients to reduce pain, increase healing and rehabilitation.

A VRB fixed at one or more points acts as a cantilever to selectively unload or lift; while simultaneously acting as a reactive leaf spring or dynamic suspension system for the knee, proportional to the loading of the resistance setting, thereby maintaining a set separation distance for the knee joint that is dynamically controlled.

A VRB cantilever with an elastomeric material acts as a selectable dynamic suspension system with a 'secondary or artificial cartilage' shock absorber to cushion or 'catch' the VRB from bottoming out under heaviest loading compression or flooring of the cantilever.

Additionally, a novel floating hinge is employed with a VRB cantilever to provide lift, suspension and separation to the knee joint.

Additionally, an elastomeric polymer or other shock absorbing energy returning material acts as a secondary cartilage in conjunction with a VRB. The shock absorbing material acts as a standalone and/or redundant back up to cushion and absorb impact loads that supersede the selected VRB suspension or mechanical limit of the VRB to support load.

The dynamically unloading knee brace provides prescriptive lift, suspension and separation for OsteoArthritc, Postoperative, rehabilitative and prophylactic patients, as well as military field applications.

Dynamic Tension is achieved by selecting/setting resistance levels to impart corrective structural bias and or compensating support for a damaged joint.

According to the principles of the invention, redistribution of load and support of the patello-fermoral knee joint is applicable to provide flexibility of the joint for exercise activities such as walking, hiking, running and carrying additional pack weight.

In accordance with the principles of the invention, the brace system disclosed can also be used or integrated as a stand-alone modular unit or as part of an exoskeletal support system mechanically linked to a backpack, for example, and furthermore to a knee brace and the knee brace to an ankle support and ultimately to an orthotic or all terrain boot or footwear.

In accordance with the principles of the invention, the bushings act as a second knee cartilage. In accordance with the principles of the invention, the bushing or shock material may be a flexible material, such as rubber, elastomer or similar shock absorbing and energy releasing material.

In another aspect, the bushing may be of a mechanical construction.

A feature of an adjuster mechanism with indicia enables the wearer to 'pre-load' the VRB or bushing assembly by compressing the VRB against the vertical weight of the body. This provides lift or separation to the patello-fermoral joint to maximize comfort, brace fit and weight unloading to the knee joint for each individual's knee, injury or weakness, and pack weight, by incrementally vertically extending the floating hinge, lifting the upper leg/quadriceps.

The bushings have a range of Shore A durometers to adjust for 'road feel' or ergonomic comfort against body/pack weight. The bushing material may also be multi-layered to impart performance advantages a single material or mechanical construction could not provide.

In one aspect of the invention, the VRB or the bushing assembly's mechanical movement can be used as a battery recharging system using any device capable of capturing mechanical movement and converting the mechanical movement into electrical energy. For example, piezo-material or PvF2 (PolyVinylidene Fluoride 2) may be incorporated into the bushing assembly to create a battery recharging system.

In accordance with the principles of the invention, ergonomic, conformal and/or conical sectioned cup pads (hereinafter, pads) may be incorporated to assist the brace's retention of the quadriceps and calf muscles to ensure a positive positioning lock and enhance comfort. This is particular beneficial as muscle swelling and constriction occurs during hiking or extended periods of use.

In accordance with the principles of the invention, the conformal geometric/ergonomic plates are used to distribute load (i.e., the body's weight) over a greater surface area to increase comfort and hold or retain the brace in place. In addition, the conformal geometric plates may be perforated or breathable to allow perspiration to be drawn away from the skin.

In accordance with the principles of the invention, the plates can be ballistic protection for applications that are highly dangerous. For example, military and/or police operations.

In accordance with the principles of the invention, an optional knee pad may be incorporated to protect the kneecap or patella.

In accordance with the principles of the invention, the knee brace uses a floating hinge assembly to maximize shock absorption, energy return, comfort and natural knee movement.

In accordance with the principles of the invention, hyperextension selectable stops may be incorporated in order to protect the joint (e.g., knee) under load from hyper-extending.

In accordance with the principles of the invention, the exoskeleton brace disclosed provides for silent operation in an ultra-light weight configuration (aluminum, carbon fiber) that provides medial and lateral support (particular for the knee).

BRIEF DESCRIPTION OF THE DRAWINGS

The advantages, nature, and various additional features of the invention will appear more fully upon consideration of the illustrative embodiments to be described in detail in connection with accompanying drawings wherein like reference numerals are used to identify like element throughout the drawings:

FIG. 1(a) represents a Type I I-Beam configuration that is substantially circular;

FIG. 1(b) represents a Type II I-Beam configuration that includes a spline;

FIG. 1(c) represents a Type III Dual I-Beam configuration that includes an inner and outer spline;

FIG. 1(d) represents a Type IV Conical beam configuration having cut-out section;

FIG. 1(e) represents a Type V Ellipsoidal beam configuration having a major and minor axis;

FIG. 1(f) represents a Type VI Internal 'I-beam' configuration having an internal spline; and FIG. 1(g) represents a Type VII Rectangular beam configuration.

FIG. 1A(a)-(c) thru FIG. 1G(a)-(d) illustrate examples of the resilient rods in accordance with other aspect of the embodiment of the invention as shown in FIG. 1(a) thru FIG. 1(g) regarding cross-section, resistance and bending force applied to different hand positions.

FIG. 2A(a)-FIG. 2A(f) Illustrates a comparison of a symmetric or basically round and or an asymmetric or elongated cross sectional rod held at two positions.

for symmetric or basically round (1 set) and (2 set) asymmetric or elongated cross sections.

Figure 4:
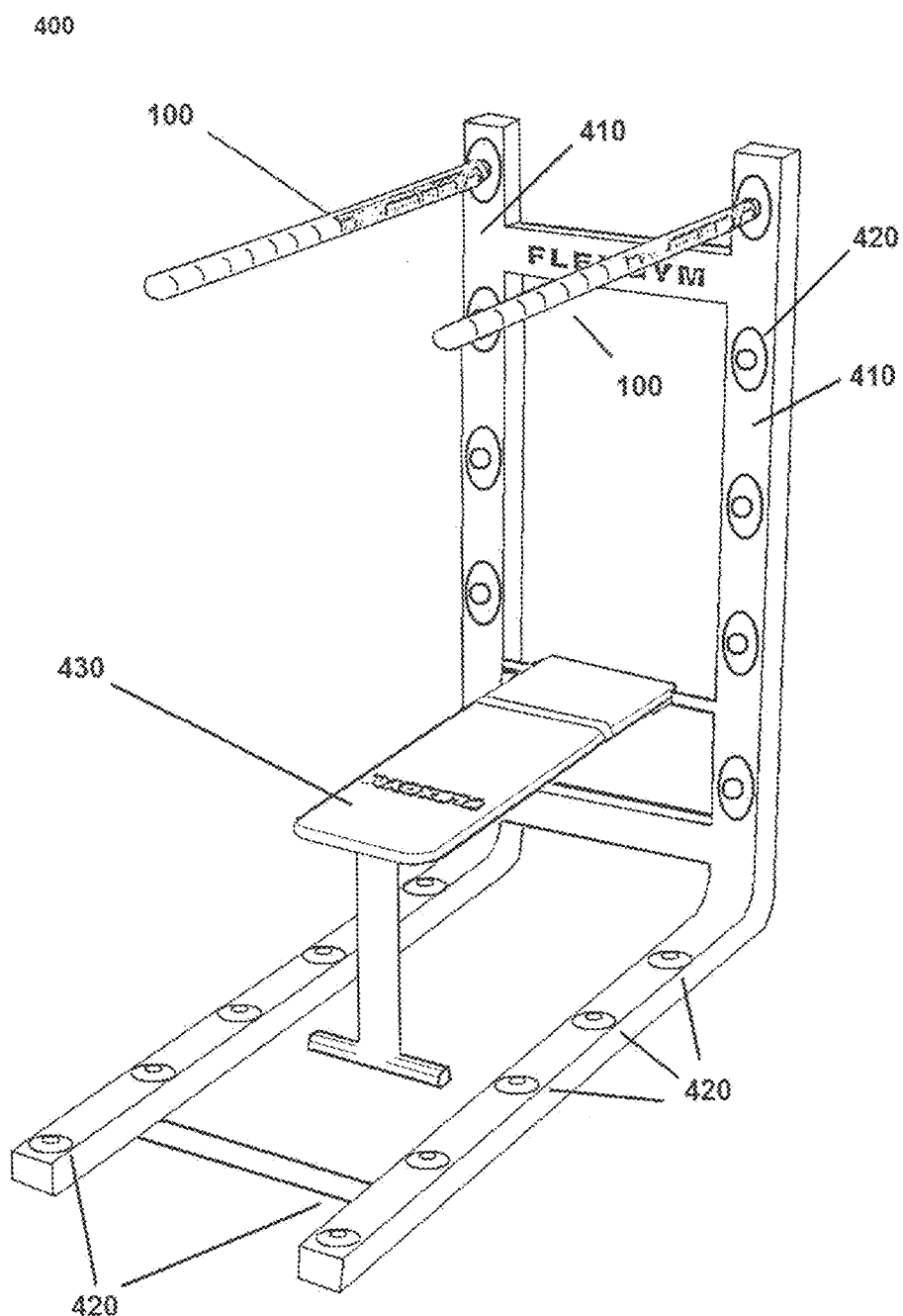

FIG. 4 illustrates an exemplary exercise system configuration in accordance with the principles of the invention that incorporate a plurality of rod holders or anchors affixed along a track or tracks that are designed for the rods to be inserted into and held in place during exercise. The rod holders are designed to increase exercise efficiency by ergonomic utility or facilitate a quick change over of rods that have a higher or lower resistance range.

Figure 5:
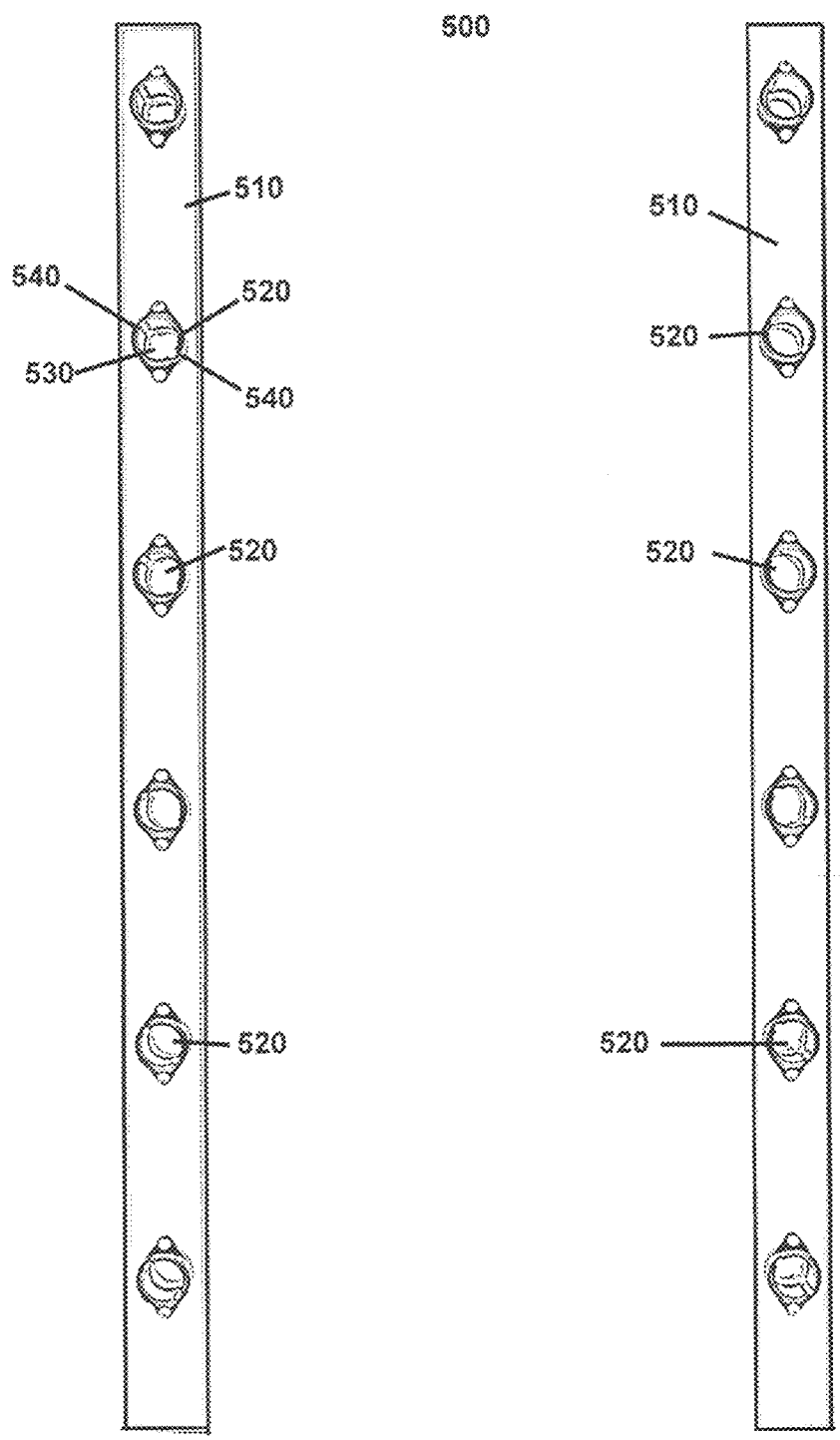

FIG. 5 illustrates an exemplary exercise system configuration of linear rigid tracks affixed with a plurality rod holders designed for the rods to be inserted into and held in place during exercise.

Figure 6:
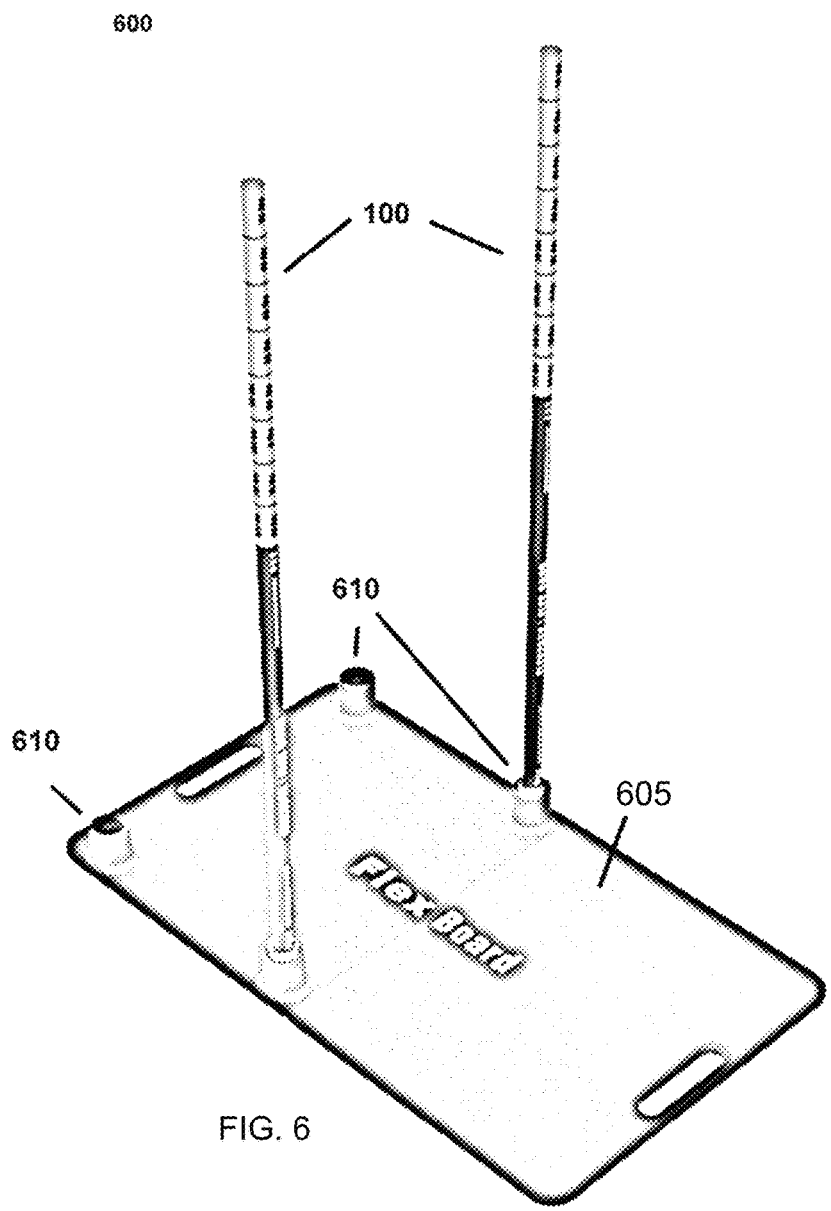

FIG. 6 illustrates an exemplary and portable exercise system configuration in accordance with the principles of the invention comprised of a folding flat workout surface, with a plurality of perpendicular rod holders designed for the rods to be inserted into and held in place during standing exercises.

Figure 7:
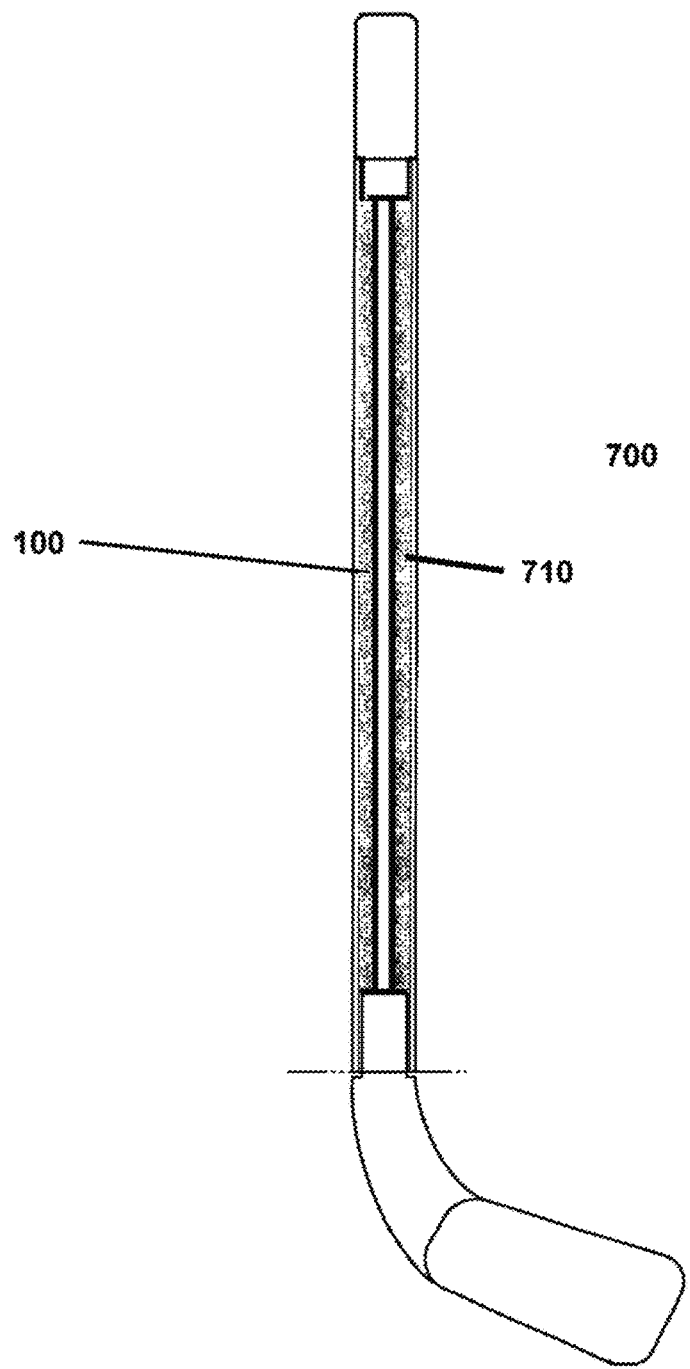

FIG. 7 illustrates an exemplary sports equipment configuration for a resistance beam centrally located within a solid wooden or hollow aluminum or graphite shaft of a hockey stick in accordance with the principles of the invention.

Figure 8:
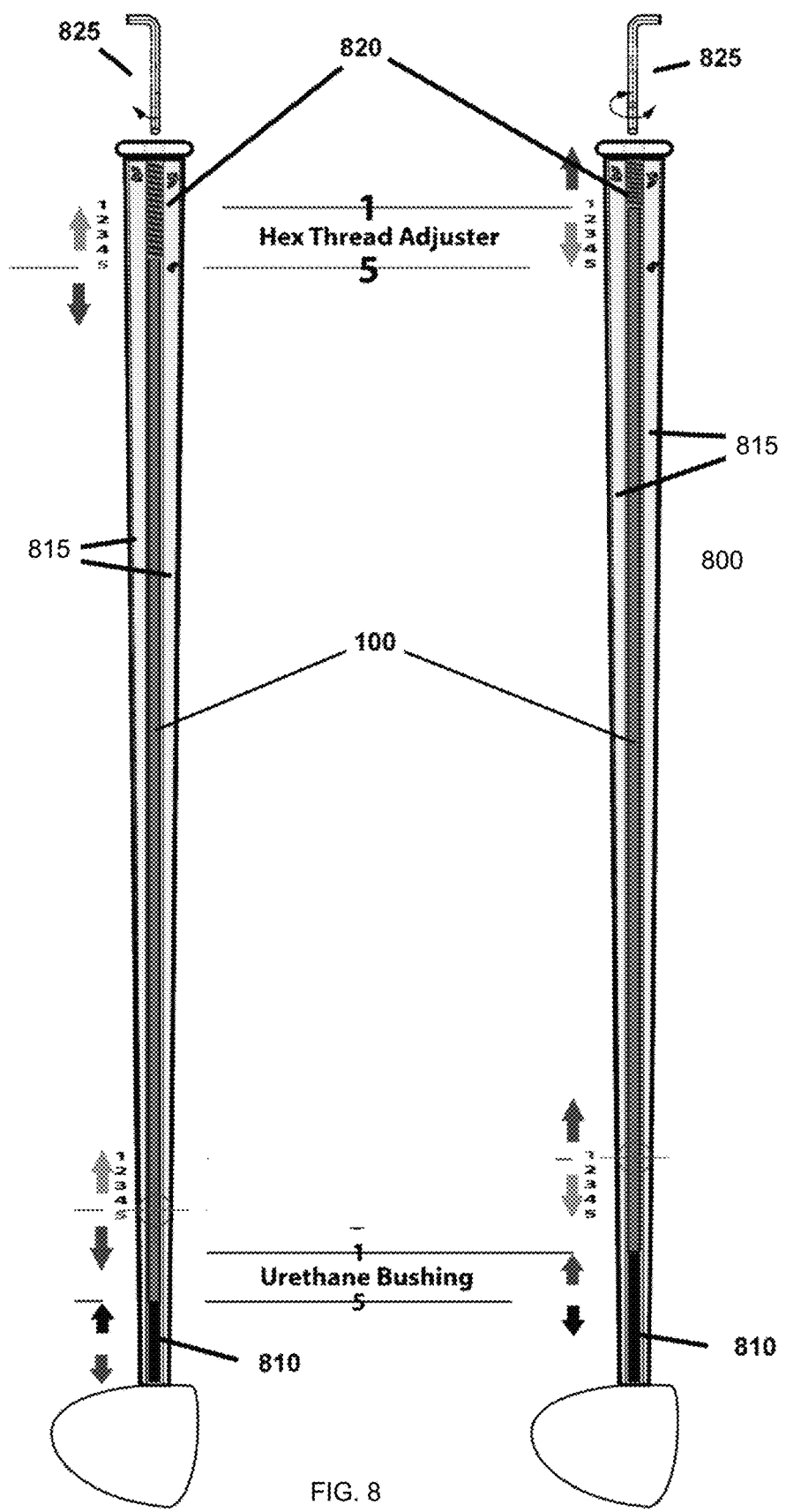

FIG. 8 illustrates an exemplary beam mechanically positioned centrally within a golf shaft configuration in accordance with the principles of the invention.

Figure 9:
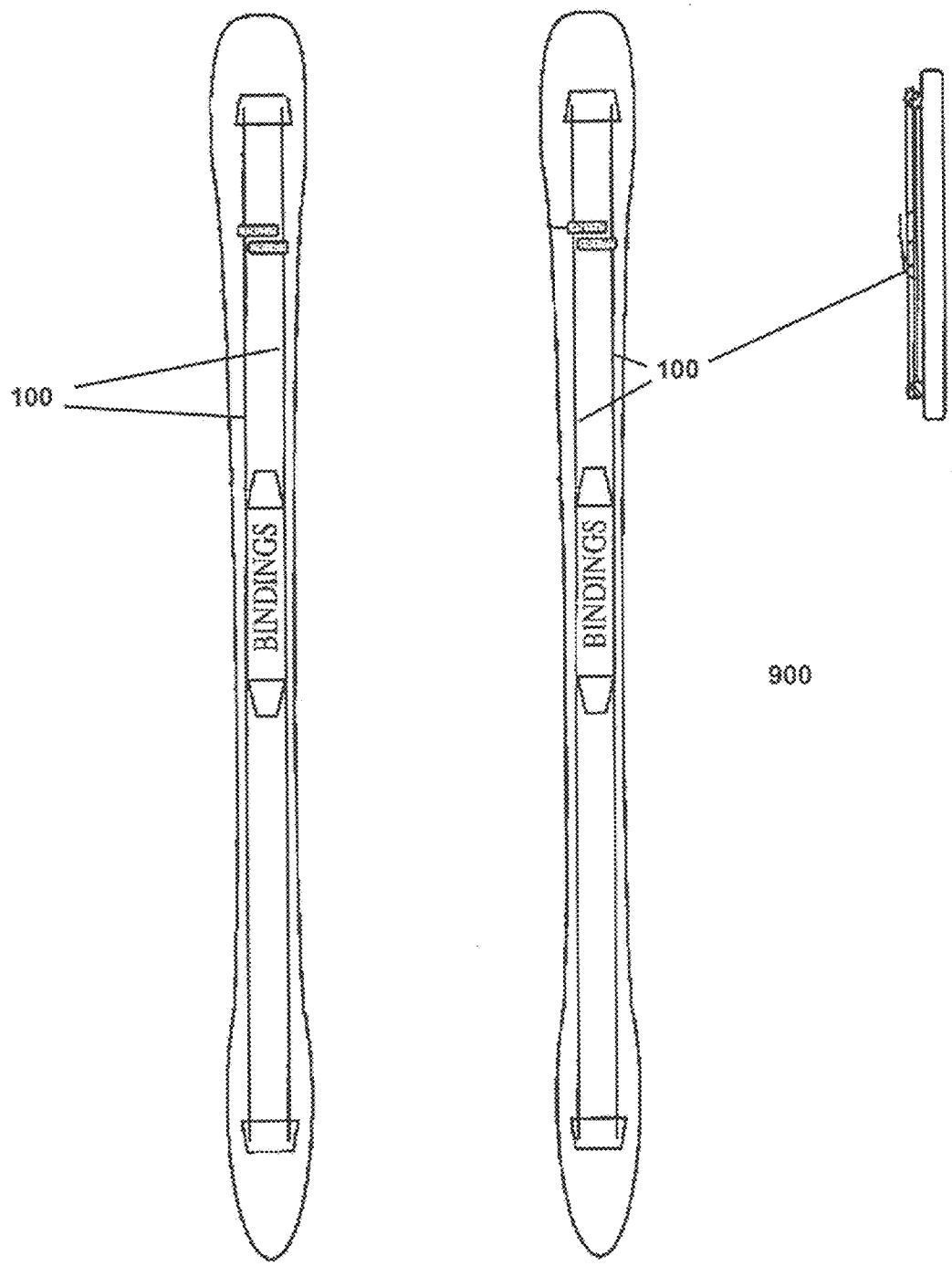

FIG. 9 illustrates an exemplary ski sports equipment configuration with an adjustable resistance beam that imparts a resistance range along the length of the body of the ski in accordance with the principles of the invention.

Figure 10A:
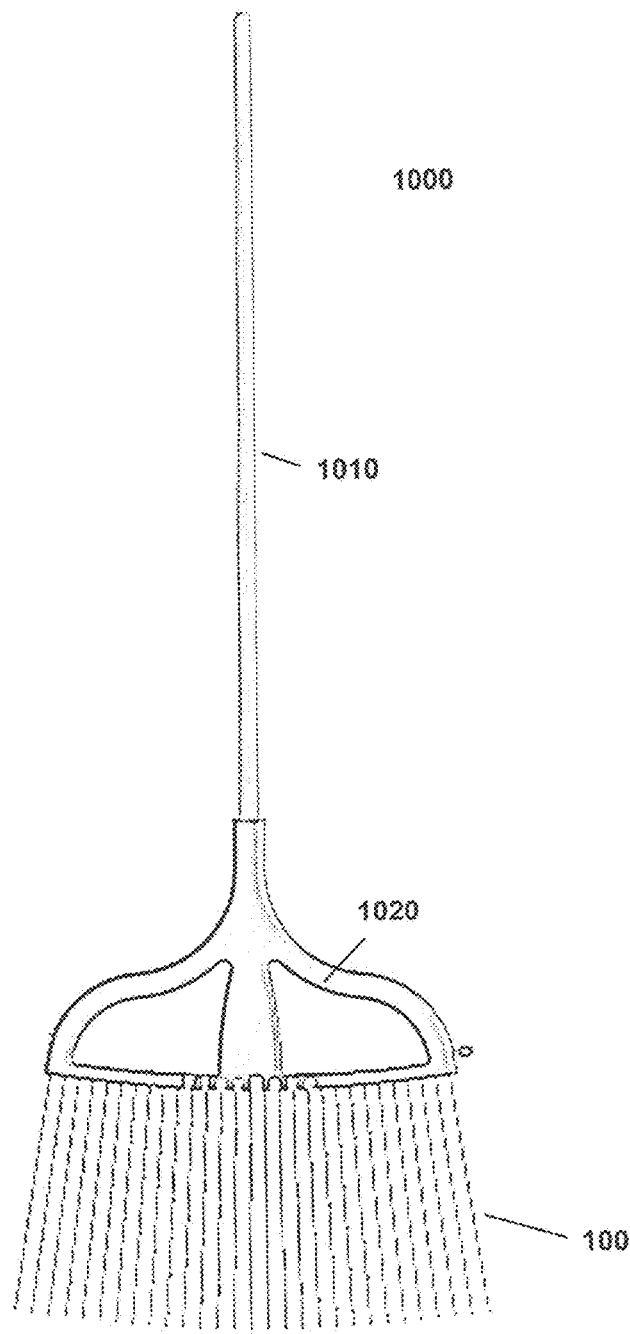
Figure 10B:
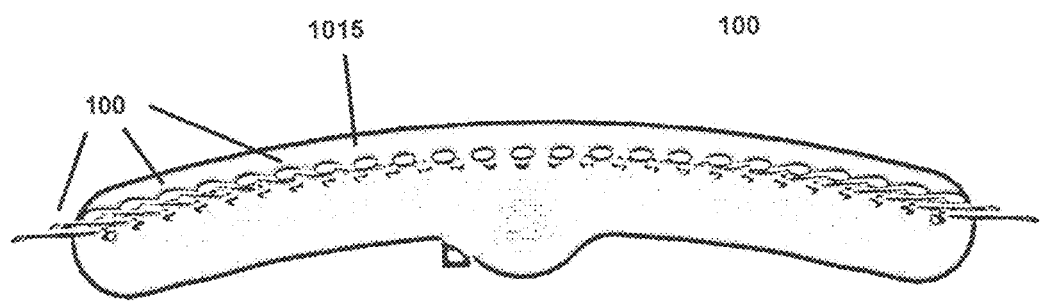

FIG. 10A-FIG. 10B illustrate exemplary configurations of a lawn device configured in accordance with the principles of the invention. The tines of this adjustable flex rake are individual resistance beams that are simultaneously rotated.

Figure 11:
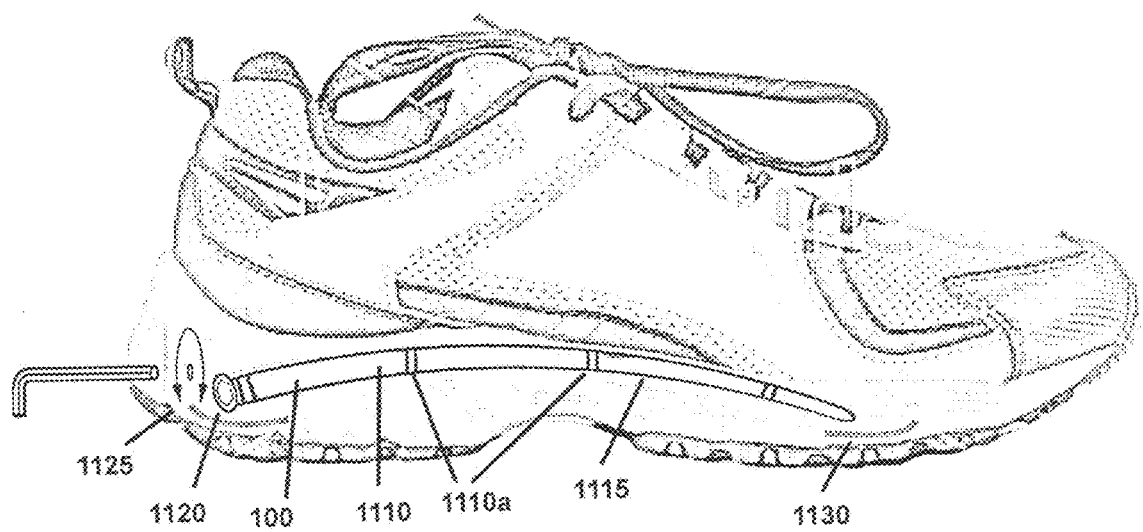

FIG. 11 illustrates an exemplary adjustable active suspension system configuration for sports footwear in accordance with the principles of the invention.

Figure 12:
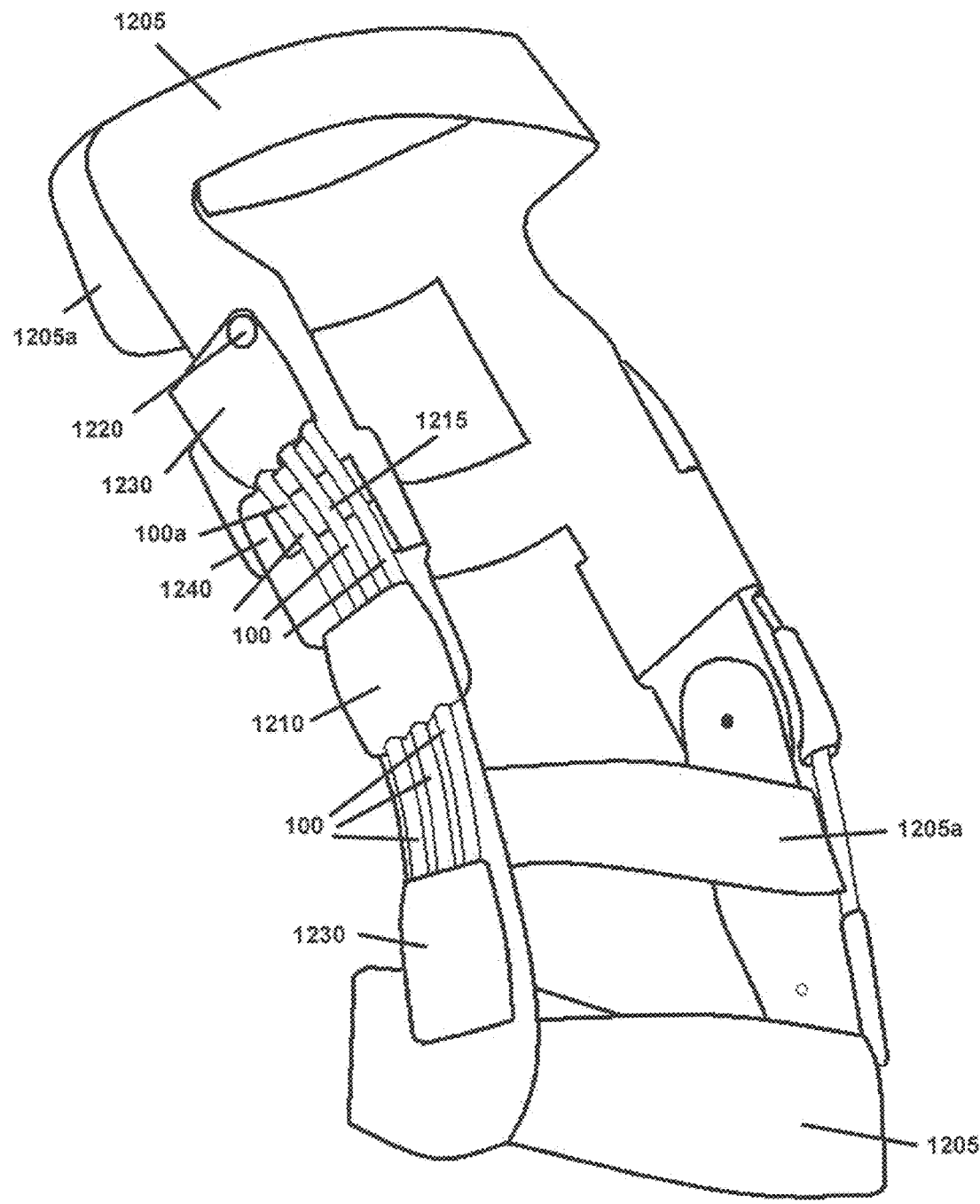

FIG. 12 illustrates an exemplary medical device configured in accordance with the principles of the invention. The resistance beams are employed into mobility assistance and rehabilitative braces that provide dynamic support and suspension via a fulcrum mechanism.

Figure 13A:
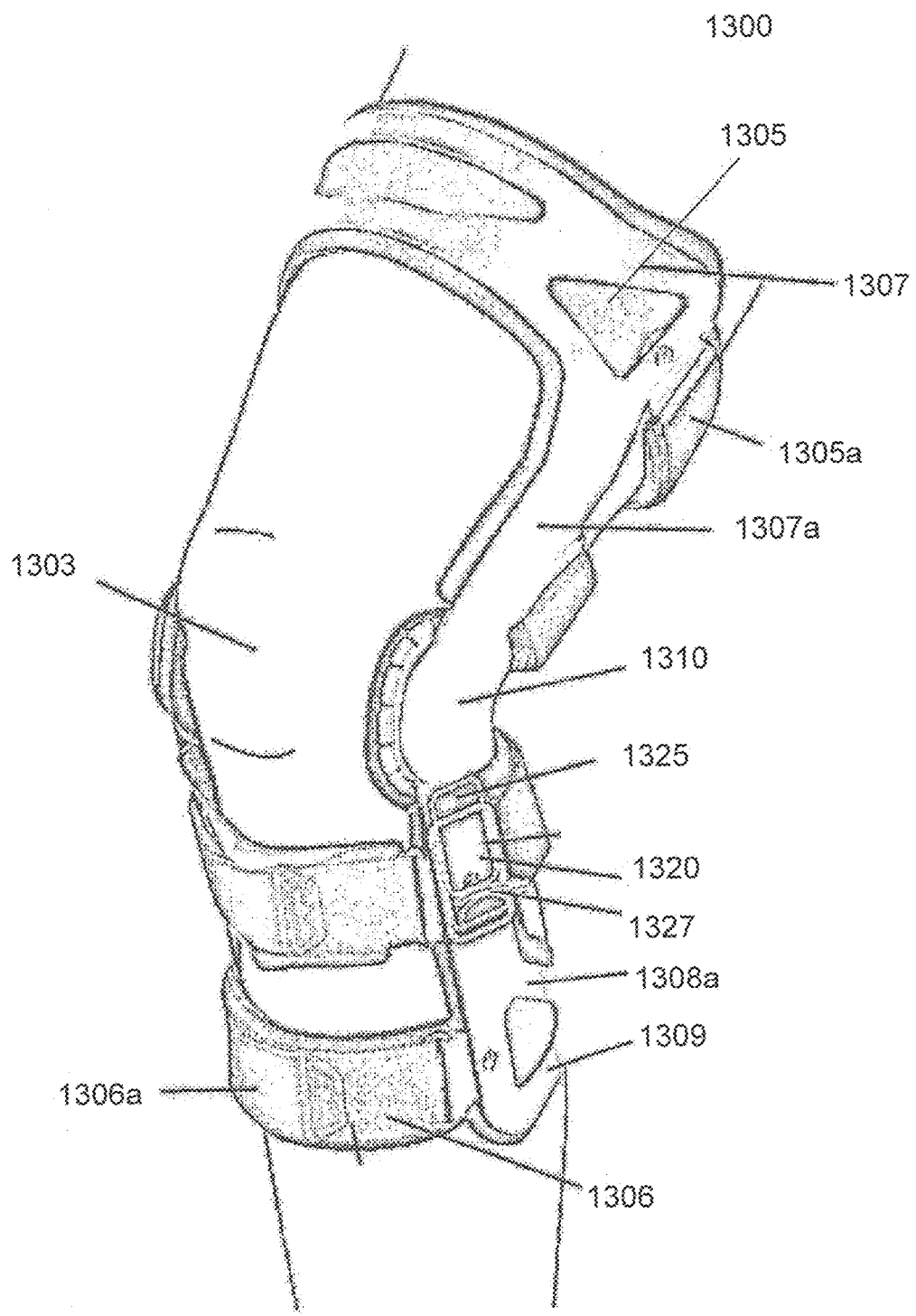

FIG. 13A illustrates a perspective view of an exemplary embodiment of a knee brace in accordance with the principles of the invention.

Figure 13B:
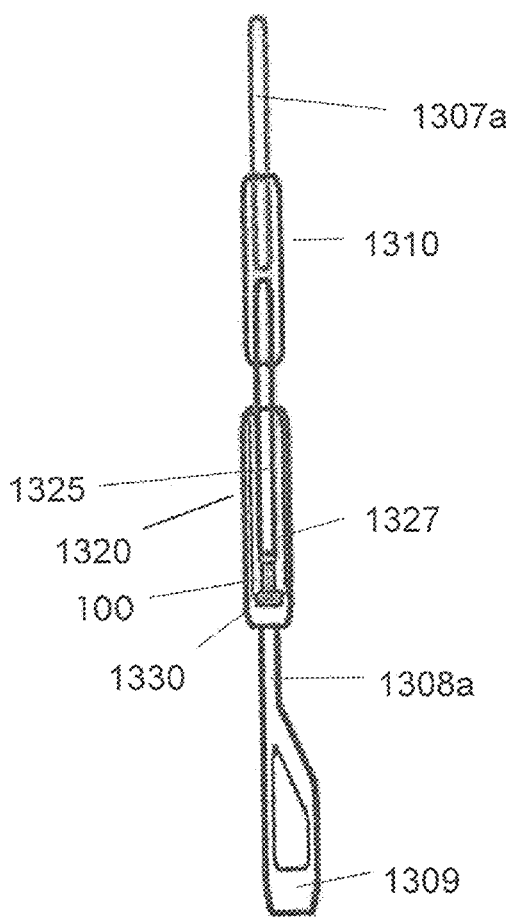

FIG. 13B illustrates a side view of a polycyclic gear in accordance with the principles of the invention.

Figure 2:
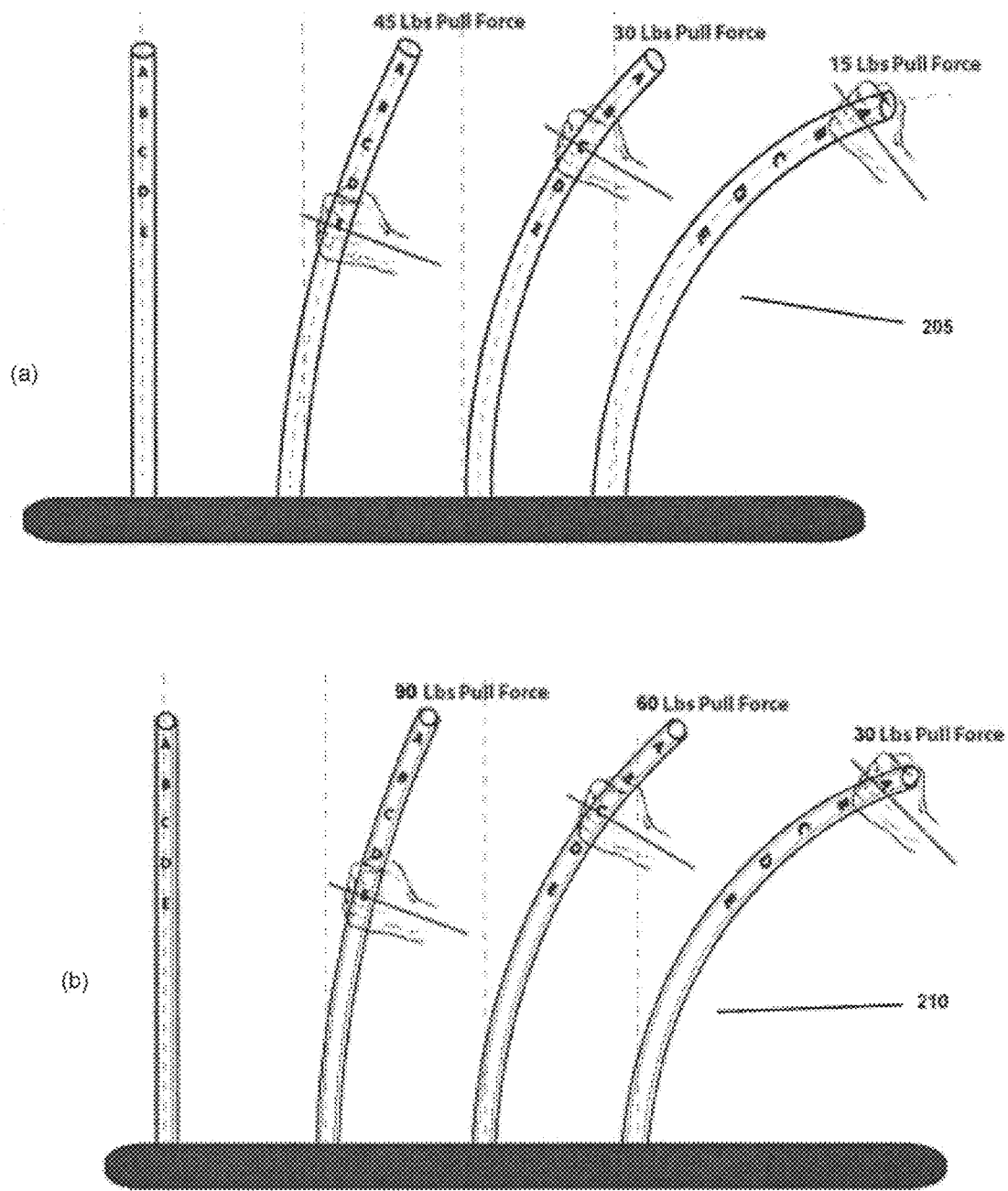
FIG. 2(a) and FIG. 2(b) illustrate a comparison of a symmetric or basically round and an asymmetric or elongated cross sectional resistances generated by each type of rod with the same hand position indicia.
Figure 14A:
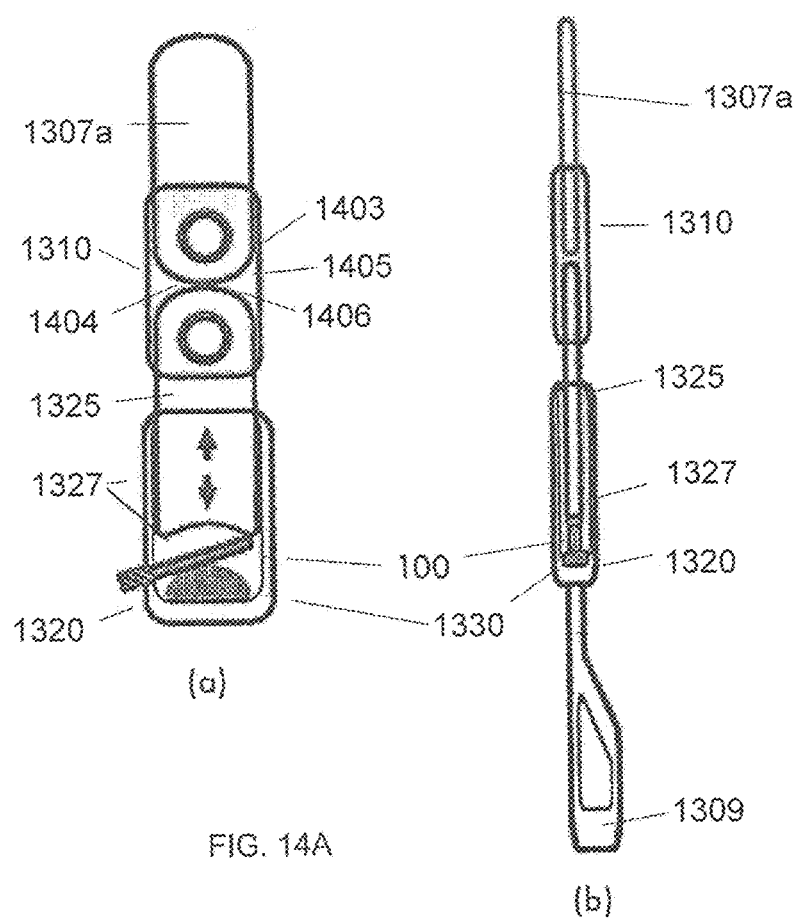
Figure 14B:
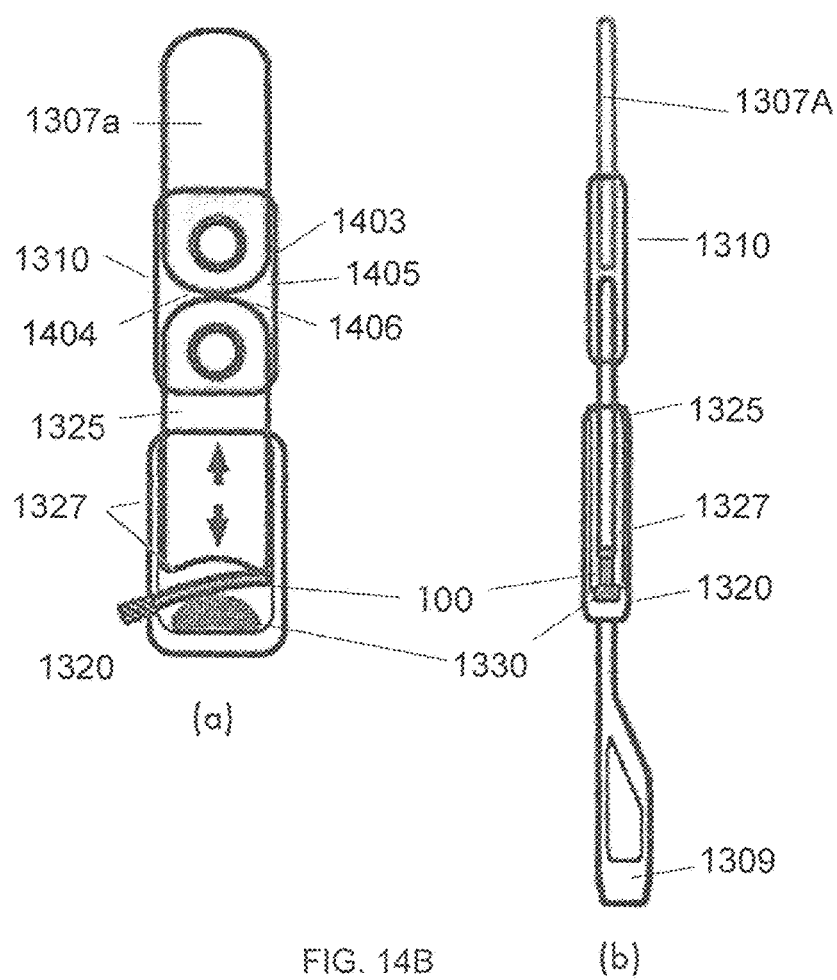
Figure 14C:
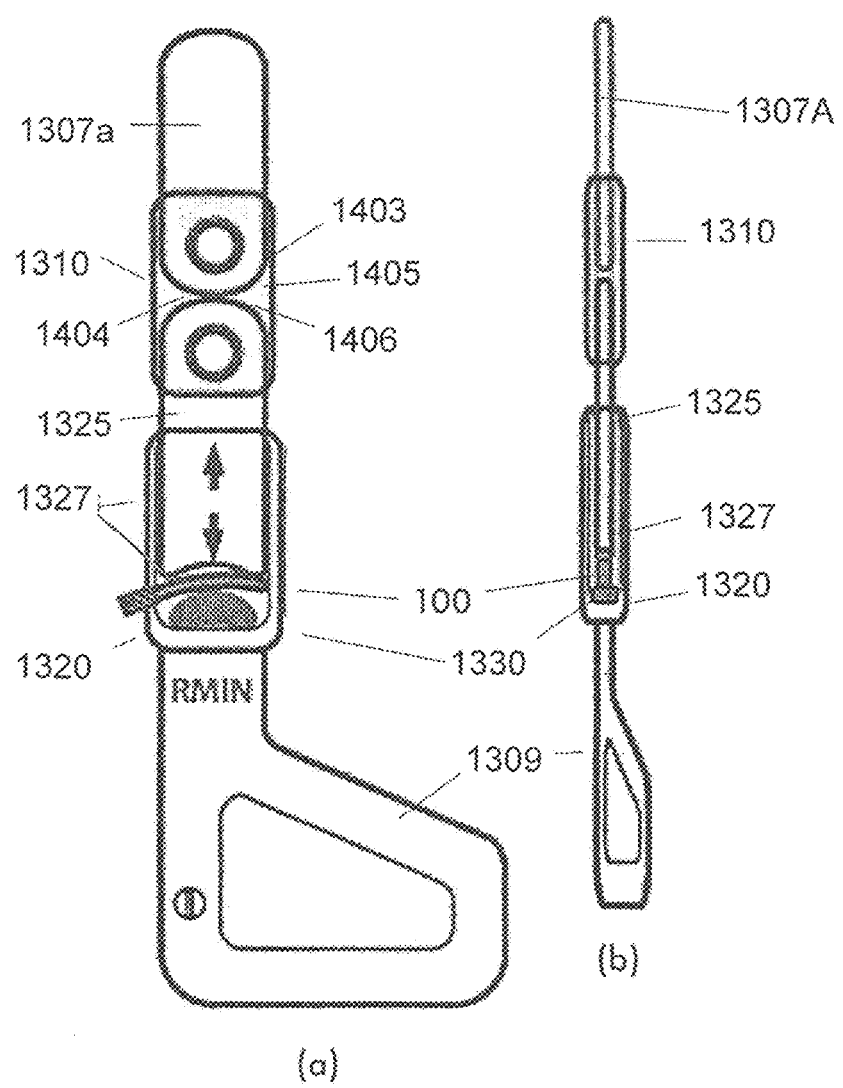

FIG. 14A(a)-(b)-FIG. 14C(a)-(b) illustrate an exemplary mechanism using VRB technology for controlling compression in the knee brace shown in FIG. 2.

FIG. 15A-FIG. 15D illustrate an exemplary configuration for controlling rotation of a VRB utilized in the knee brace shown in FIG. 2.

Figure 16:
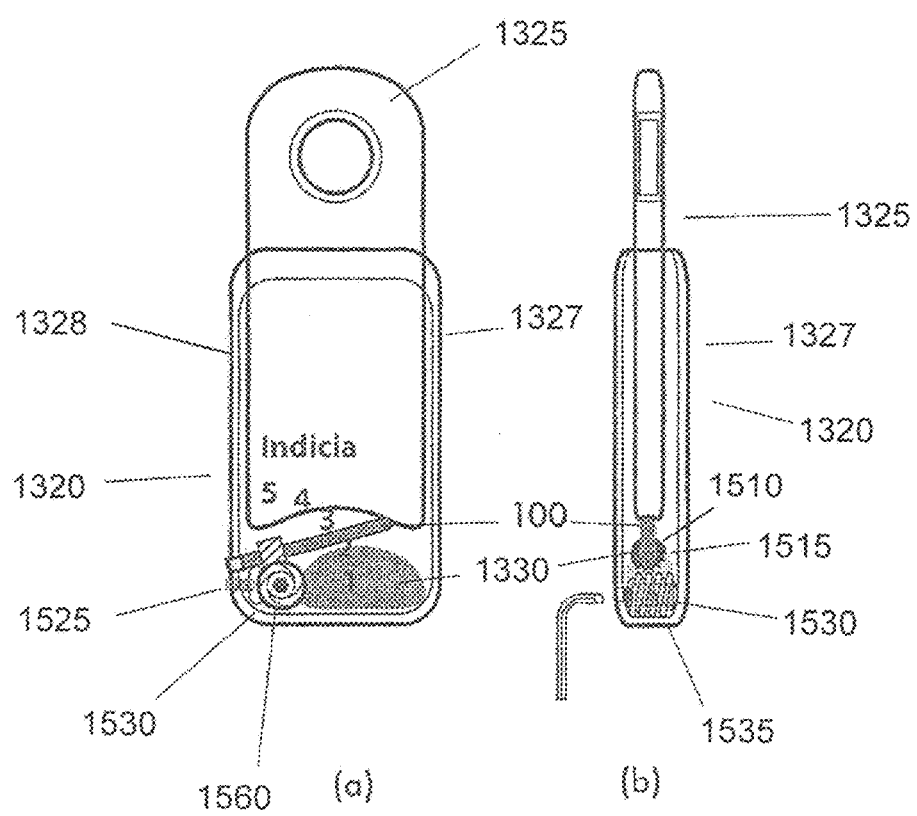

FIG. 16A-FIG. 16B illustrates a front view and a side view of a compression assembly in accordance with the principles of the invention.

Figure 17:
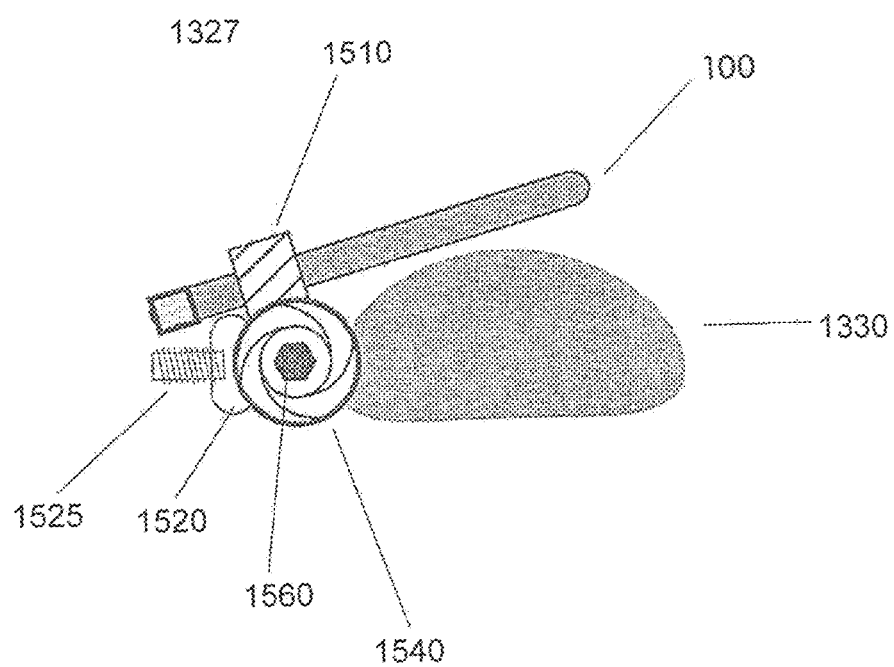

FIG. 17 illustrates a cross-section view of a compression mechanism in accordance with the principles of the invention.

Figure 18:
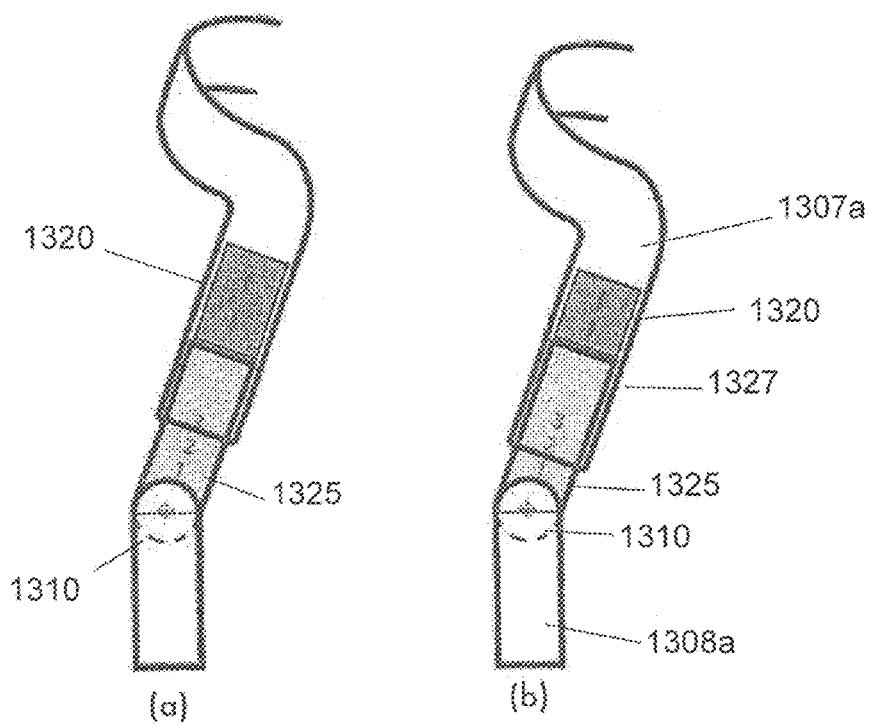

FIG. 18A-FIG. 18B illustrates a second exemplary embodiment of a knee brace in accordance with the principles of the invention.

FIG. 19A-FIG. 19E illustrate a second exemplary configuration for controlling rotation of a VRB utilized in the knee brace shown in FIG. 13A.

Figures 20A, 20B:
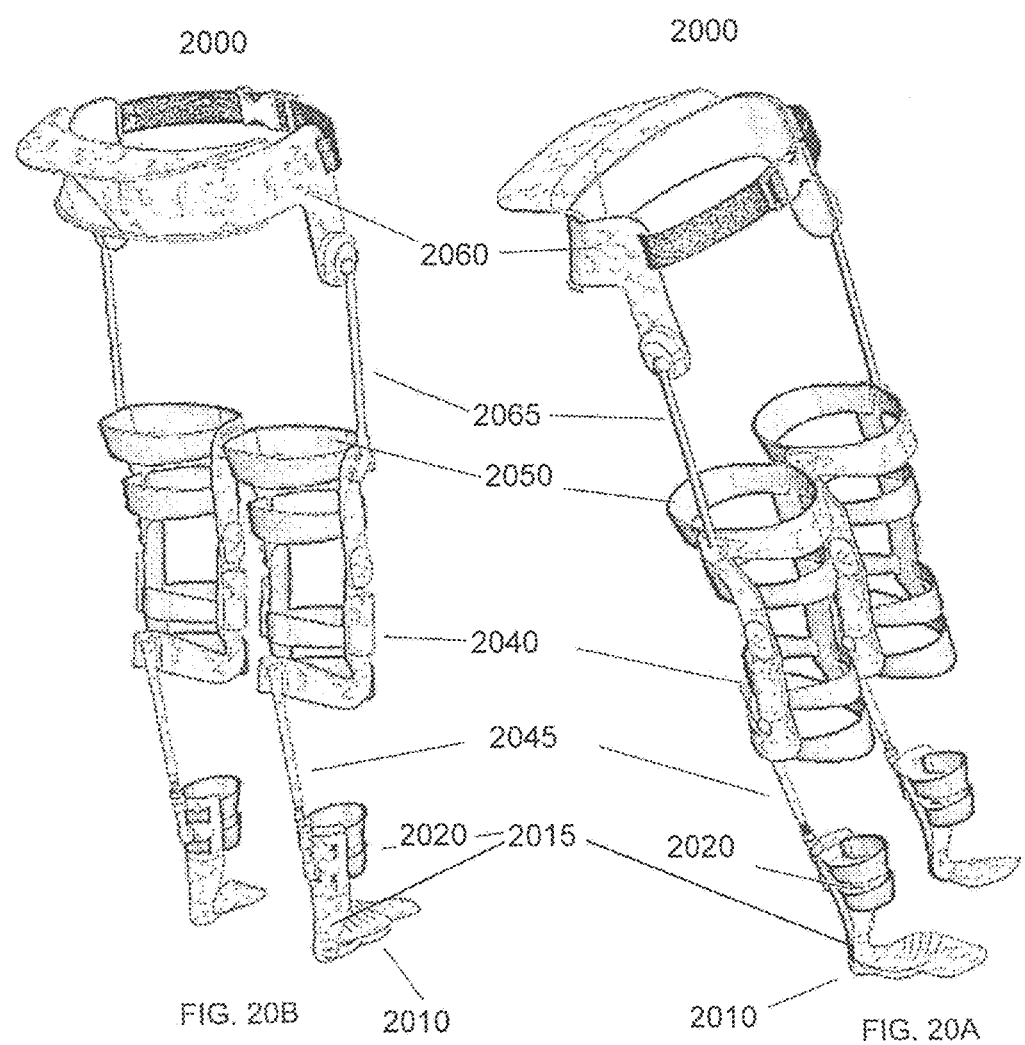

FIG. 20A and FIG. 20B illustrate perspective view of an exemplary exo skeleton body suit incorporating the knee brace shown in FIG. 13A.

It is to be understood that the figures and descriptions of the present invention described herein have been simplified to illustrate the elements that are relevant for a clear understanding of the present invention, while eliminating, for purposes of clarity many other elements. However, because these elements are well-known in the art, and because they do not facilitate a better understanding of the present invention, a discussion of such elements is not provided herein. The disclosure herein is also directed to variations and modifications known to those skilled in the art.

DETAILED DESCRIPTION OF THE INVENTION

The object of the present invention is to adjust the flexibility and thereby the resistance of a rod by hand positioning in relationship to the fulcrum of rod; or by bending a rod and spine within the shaft; or by bending a single solid rod; or both the bending of an outer beam and an inner beam in another example. This affects the longitudinal flex and the kick or hinge point of flexure where maximum flexure bending forces arise, depending on the hand position or anchor point in relationship to the fulcrum.

A shaft includes any tube-like structure by itself, attached to the outside of another surface or incorporated within a structure. Examples of a tube-like shaft by itself include hockey sticks, golf clubs, lacrosse sticks, pole vaulting poles, fishing rods, sailboard/sailboard masts, canoe/kayak paddles or oars, baseball bats, archery bows, tennis racquets and exercise machine tensioning rods. Examples of products to which a tube-like shaft might be attached externally include skis, snowboard bindings and bicycle frames.

A beam or rod includes any solid, semi-solid or hollow elongated structure or rod, wherein the rigidity of the beam or rod is dependent at least upon the thickness of the material constructing the beam and the type of material. In the case of hollow beams or rods, the rigidity of the beam is also dependent upon the thickness of the wall forming the beam or rods and the material constructing the wall.

A spine includes any longitudinal structure whose flexure is different in one plane than another, in any increment of 0 to 90 degrees. This can be achieved using many materials. Examples of design shapes that have this property include, but are not limited to, I-beams, ovals, stars, triangles, rectangles, stacked circles, ellipses, etc. The spine may be solid or hollow in construction and utilize combinations of different materials and material thicknesses to achieve the preferred flexibility profile and characteristics.

Figure 1:
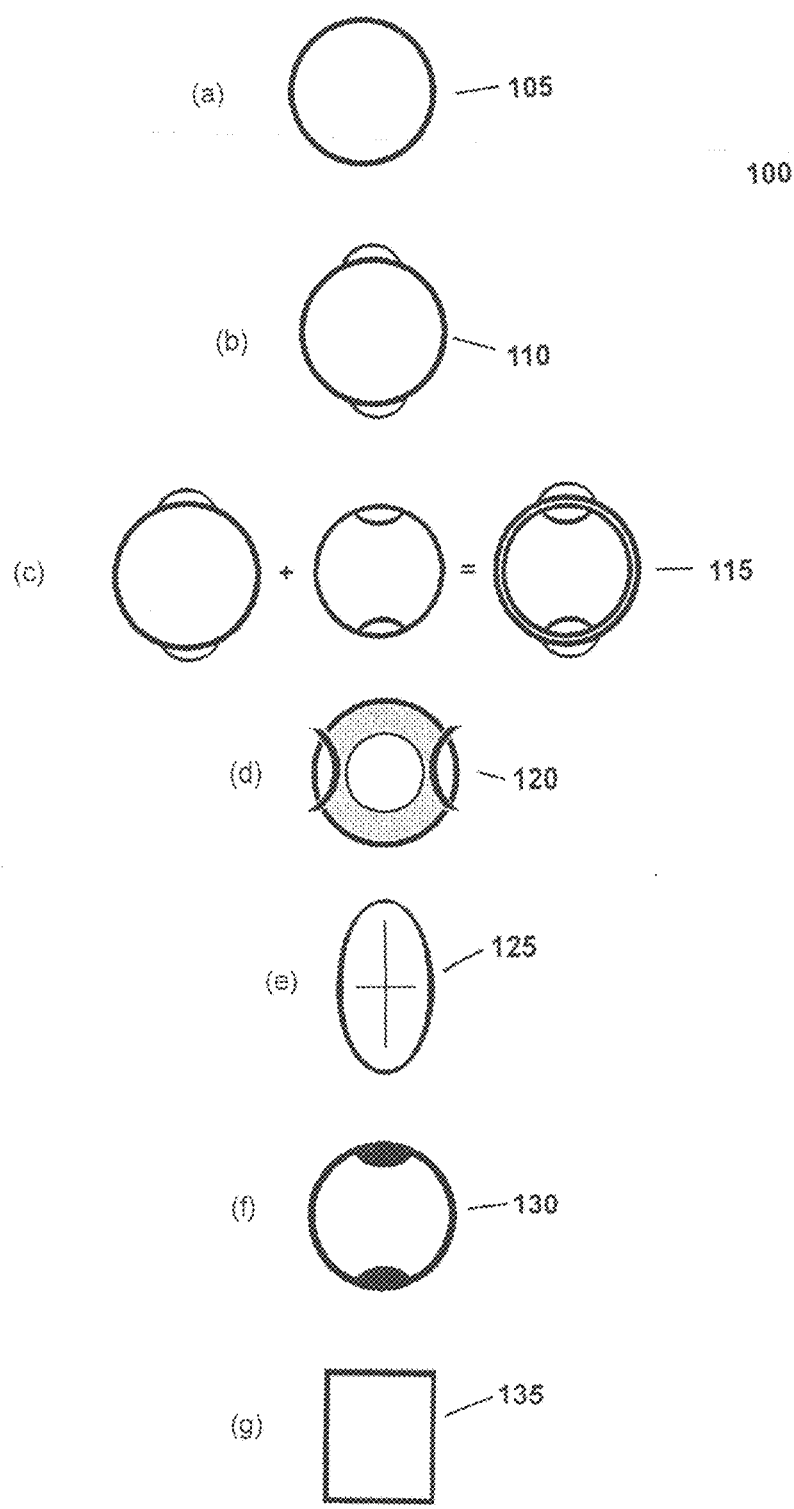
FIG. 1(a)-FIG. 1(g) represents exemplary views and cross sections of resilient rods, beams or shafts of solid, semi-solid or hollow construction in accordance with a first aspect of the invention that produce resistance and variable resistances when orientated in a direction of x, y, z plane or combination of planes in 360 degrees of rotation or bending movement.

FIG. 1 represents exemplary views and cross sections of resilient rods, beams or shafts of solid, semi-solid or hollow construction in accordance with embodiment a first aspect of the invention that produce resistance and variable resistances when orientated in a direction of x, y, z plane or combination of planes in 360 degrees of rotation or bending movement.

FIG. 1 illustrates exemplary embodiments of the invention claimed, wherein;

Type I (FIG. 1(*a*)): Non-I-Beam: includes a circular cross-section having no outside or internal diameter geometry that would create an I-beam effect: Unlike a single static rod that is intended to produce a single measurement of static resistance, fulcrum adjustable resistance is relative and proportional to hand position as indicated by an indicia zone indicated by graphics, ergonomic ridges, structures, textures and or zones of color.

Type II (FIG. 1(*b*)): I-Beam includes one of: static outside and/or internal diameter geometry or combination, thereof: I-Beam cross section geometry produces proportional adjustable resistance to rotated orientation: Geometric relationship to resistance.

Type III (FIG. 1(*c*)): Dual I-Beam: includes rotating inner and outer I-Beam tubes with inner and/or outer geometry or combination thereof to create variable I-beam resistance.

Dual I-Beam cross section geometry rotated produces proportional adjustable resistance to rotated orientation: Geometric relationship to resistance.

Type IV (FIG. 1(*d*)): Conical beam with hollow, additive or subtractive wall geometry: Conical Beam cross section geometry produces proportional adjustable resistance to rotated orientation: Geometric relationship to resistance.

Type V (FIG. 1(*e*)): Ellipsoidal beam: solid, semi-solid or hollow beam with or without outside and/or internal diameter geometry or combination, thereof along its major axis generating additional I-beam mechanics and/or subtractive, e.g., conical hollow, geometry along its minor axis. Ellipsoidal beam with a major axis that is wider than the minor axis with or without internal or external geometry along the major axis.

Type VI (FIG. 1(*f*)): Internal Spine 'I-beam' with one or more spines within a hollow cylindrical or conical shaft.

Type VII (FIG. 1(*g*)): Rectangular beam with two sides wider than the remaining two sides.

More detail description of the different embodiments of the invention are further illustrated in FIG. 1A-FIG. 1G.

Figure 1A:
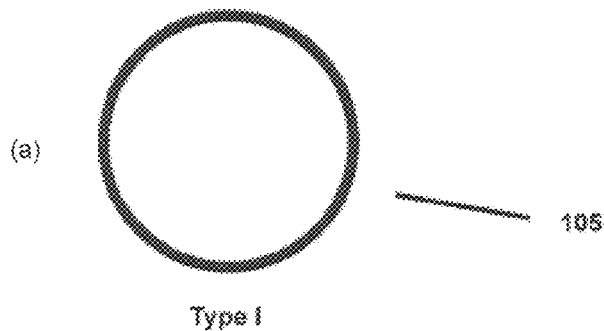
Figure 1A:
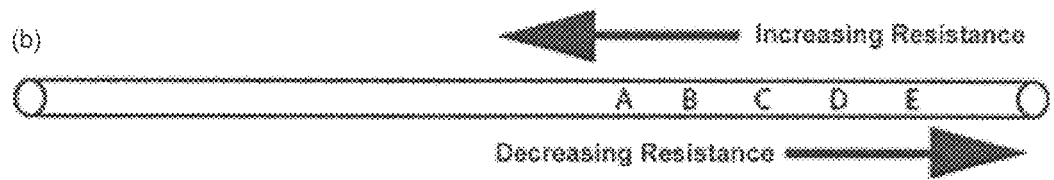
Figure 1A:
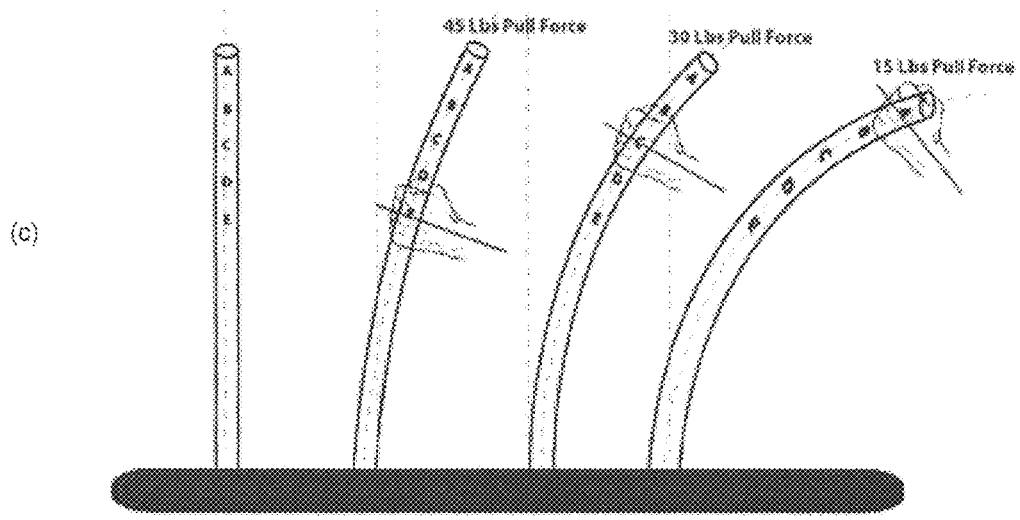

FIG. 1A (a)-(c) illustrates an exemplary embodiment of a type I VRB (variable resistance beam) 100 having a circular cross-sectional area 105 (FIG. 1A(a)). Also illustrated, FIG. 1A(b) is an exemplary VRB 100 showing indicia indicating positions of resistance. FIG. 1A(c) illustrates a series of beams 100 having cross-sectional area 105 that demonstrates exemplary bending forces (e.g., 45 Lb, 30 Lb, 15 Lb) for changing hand placement. Each new hand position provides a different resistance such that the resistance increases as a fulcrum length, from a fixed or attached point, decreases, and in the inverse, how resistance decreases as the fulcrum length increases.

Figure 1B:
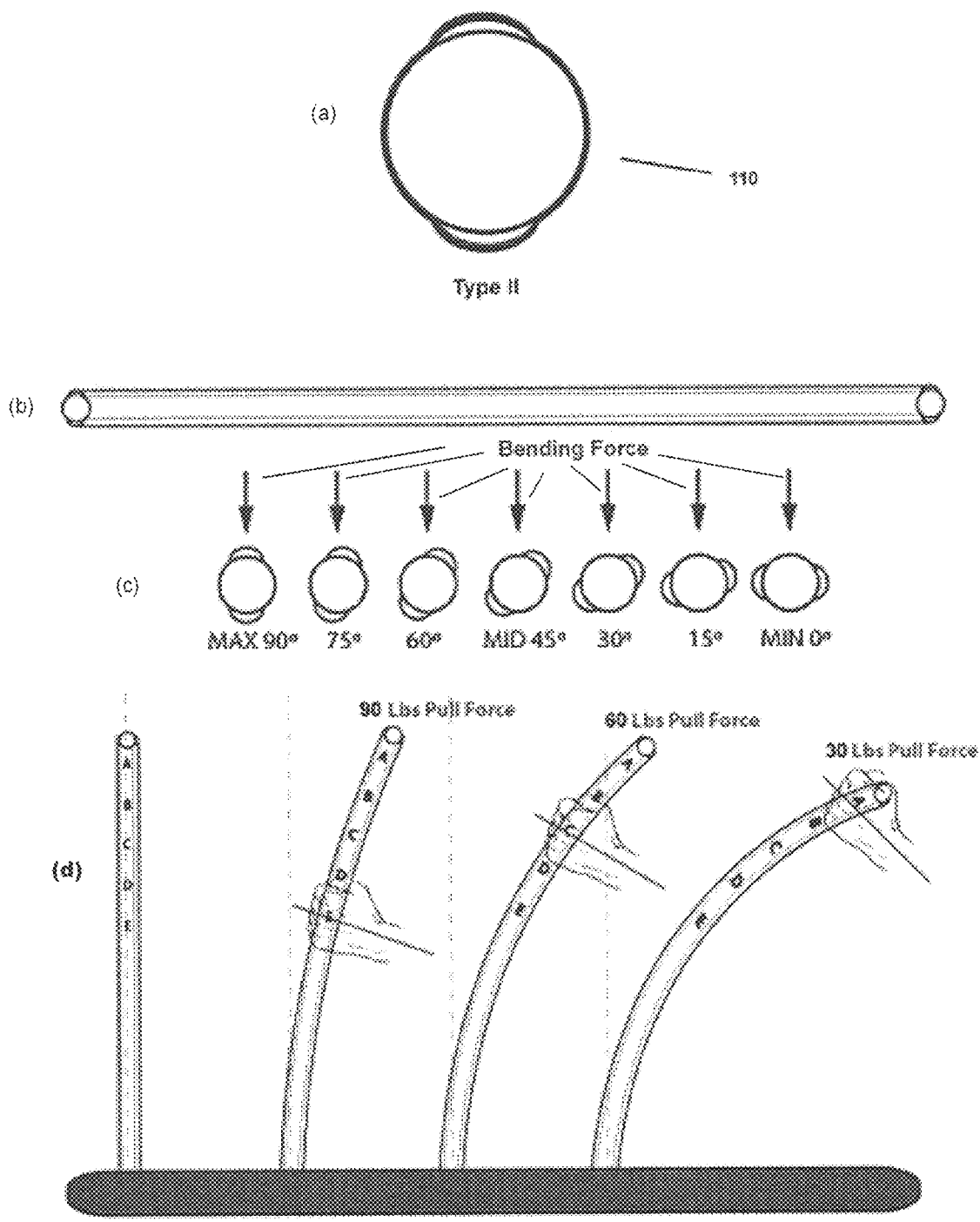

FIG. 1B(a)-(d) illustrates an exemplary embodiment of a type II VRB 100 having a circular cross-sectional area 110 including at least one outer geometric splines 112 (FIG. 1B(a). FIG. 1B(b) illustrates a prospective view of the type II VRB 110 shown in FIG. 1B(a). FIG. 1B(d) illustrates a series of VRB 100 with outer geometric spines (i.e., cross-section 110), demonstrating exemplary bending forces (e.g., 90 Lb, 60 Lb, 30 Lb) for different hand placement. Each new hand position provides a different resistance. Further illustrated is how the resistance increases as fulcrum length decreases, with respect to a fixed attachment point, and how resistance decreases as the fulcrum length increases.

FIG. 1B(c) illustrates cross sectional views of VRB 100 having cross-section 110 shown in FIG. 1B(a) at different orientations with respect to a bending force, represented by the downward pointing arrow, applied to the VRB 100 having cross-section 110, the VRB 110 as the orientation of the outer splines is rotated with respect to the illustrated bending force. In this illustrated example, the resistance to the bending force is maximum when the orientation of the outer splines is parallel to the bending force and minimum when the orientation of the outer splines is perpendicular to the bending force.

Figure 1C:
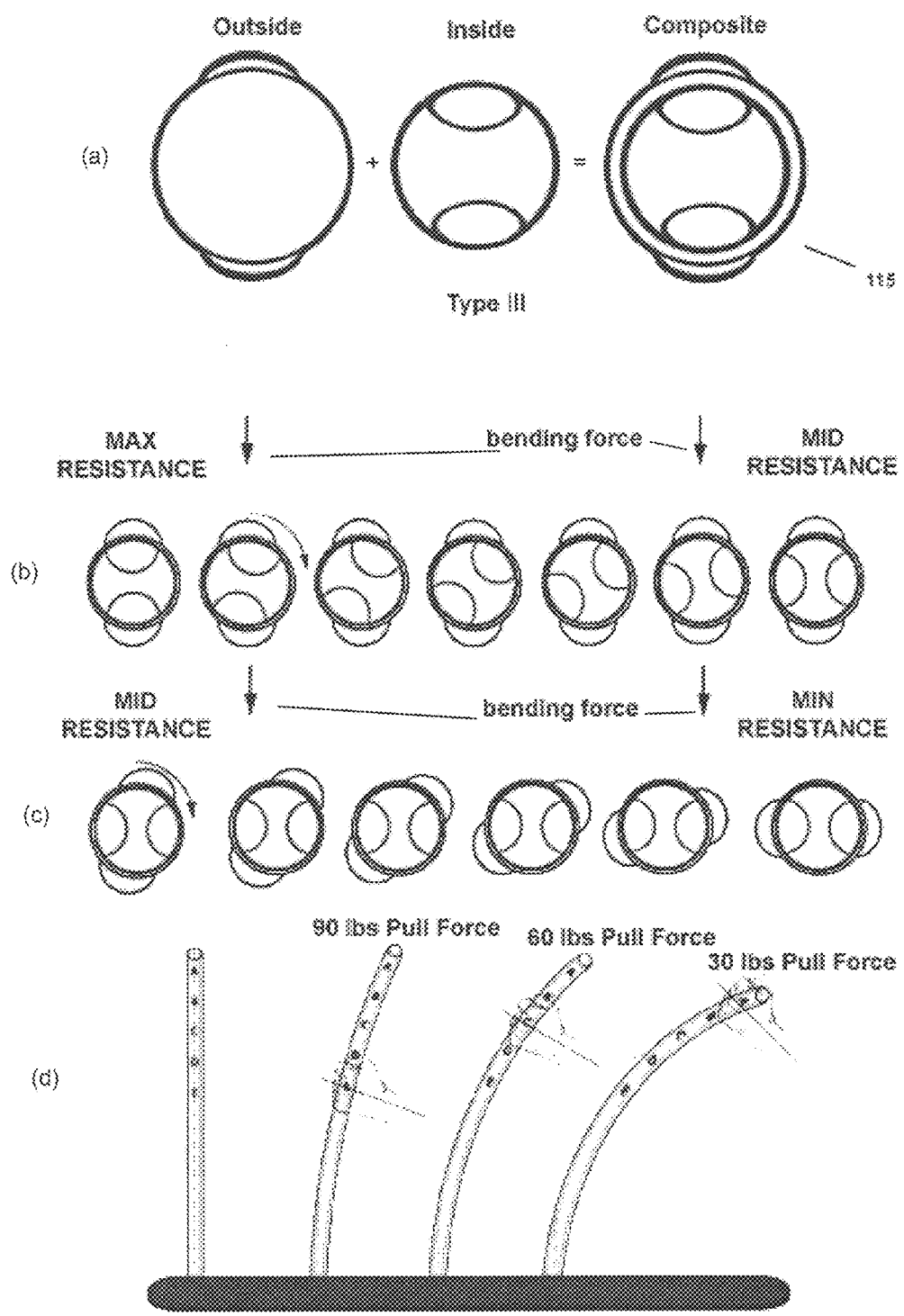

FIG. 1C (a)-(d) illustrates an exemplary embodiment of a type III VRB 100 having a cross-sectional area 115 with includes a combination of an outer shaft having external splines and an inner shaft having internal splines. That is, type III VRB 100 represents a hollow 2-cam cross section (FIG. 1C(a)). FIG. 1C(b) illustrates cross-sectional views of VRB 100 with cross sectional area 115 with respect to a bending force, illustrated as a downward pointing arrow, applied to VRB 100, wherein the inner shaft is rotated within the outer shaft. FIG. 1C(c) illustrates cross-sectional view of VRB 100 with cross-sectional area 115 with respect to the bending force wherein the outer shaft is rotated with respect to the bending force. FIG. 1C(d) illustrates a series of VRB 100 with cross-sectional area 115 demonstrating exemplary bending forces (e.g., 90 Lb, 60 Lb, 30 Lb) for different hand placement. Each new hand position provides a different resistance. Further illustrated is how the resistance increases as fulcrum length decreases with respect to a fixed attachment point, and how resistance decreases as the fulcrum length increases with respect to the fixed attachment point. Also illustrated is a change in the resistance of the type III VRB 100 as the orientation of the inner splines is rotated with respect to a bending force. In this illustrated example, the resistance to the bending force is maximum when the orientation of the inner splines is parallel to the bending force and minimum when the orientation of the inner splines is perpendicular to the bending force.

Figure 1D:
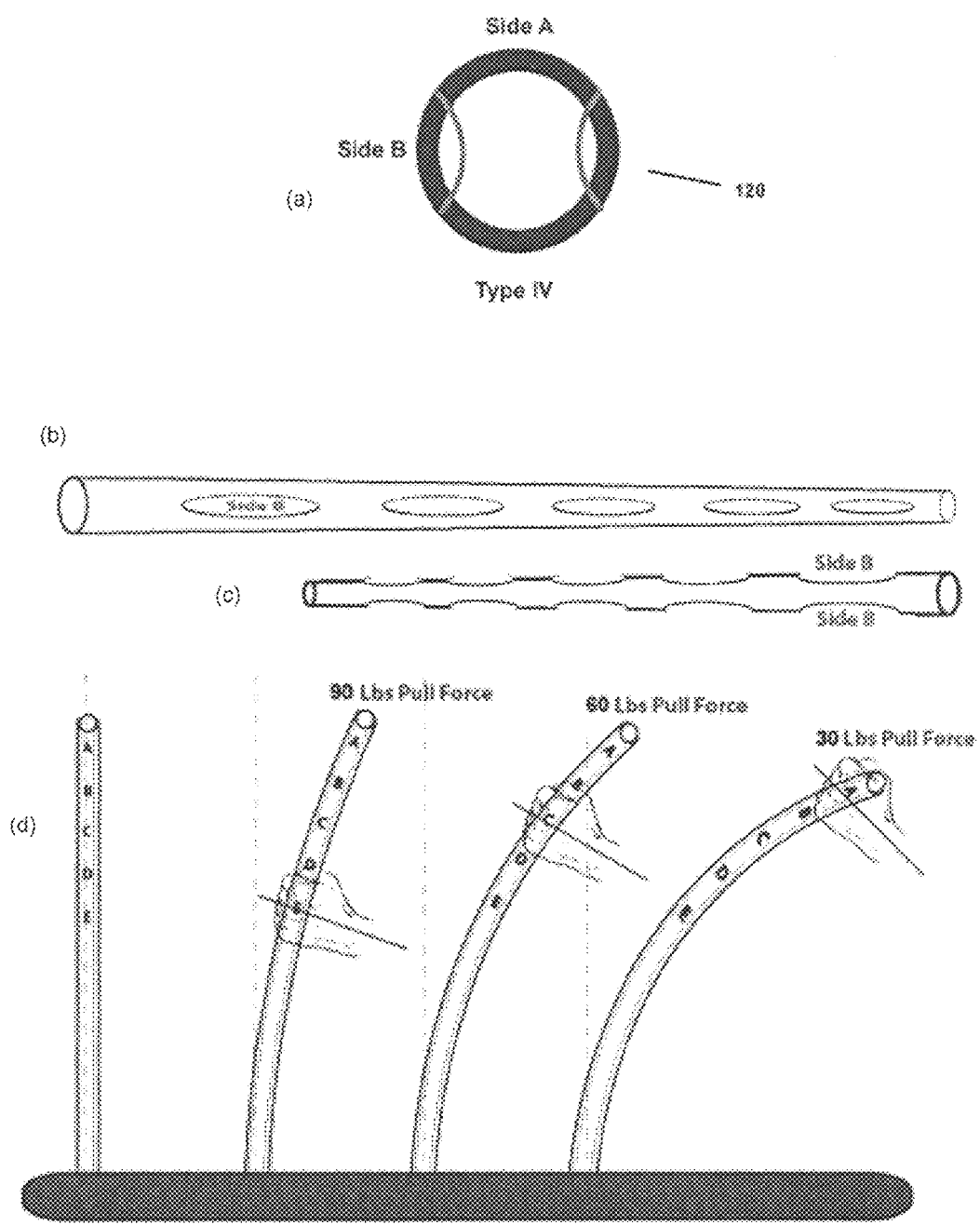

FIG. 1D (a)-(d) illustrates an exemplary embodiment of a type IV VRB 100 wherein at least one elliptical section is removed forming cross section 120 (FIG. 1D(a)). In this illustrative example, the reference Side B represents an area within the type IV VRB 100 that is removed from the VRB. FIG. 1D(b) illustrates a side views of type IV VRB 100 with cross-sectional area 120 illustrating the removal of area referred to as Side B from the type IV VRB 100. FIG. 1D(c) illustrates a cross sectional area 120 of type IV VRB 100, with cross-sectional view 120 showing elliptical scallop cuts along the inner rod or shaft. FIG. 1D(d) illustrates a series of VRB 100 with cross-section 120 demonstrating exemplary bending forces (e.g., 90 Lb, 60 Lb, 30 Lb) for different hand placement. Each new hand position provides a different resistance, wherein the resistance increases as a fulcrum length decreases, and decreases as the fulcrum length increases.

Figure 1E:
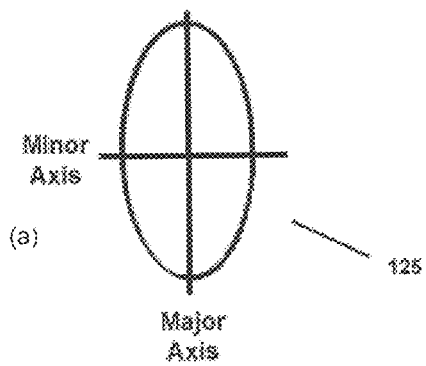
Figure 1E:
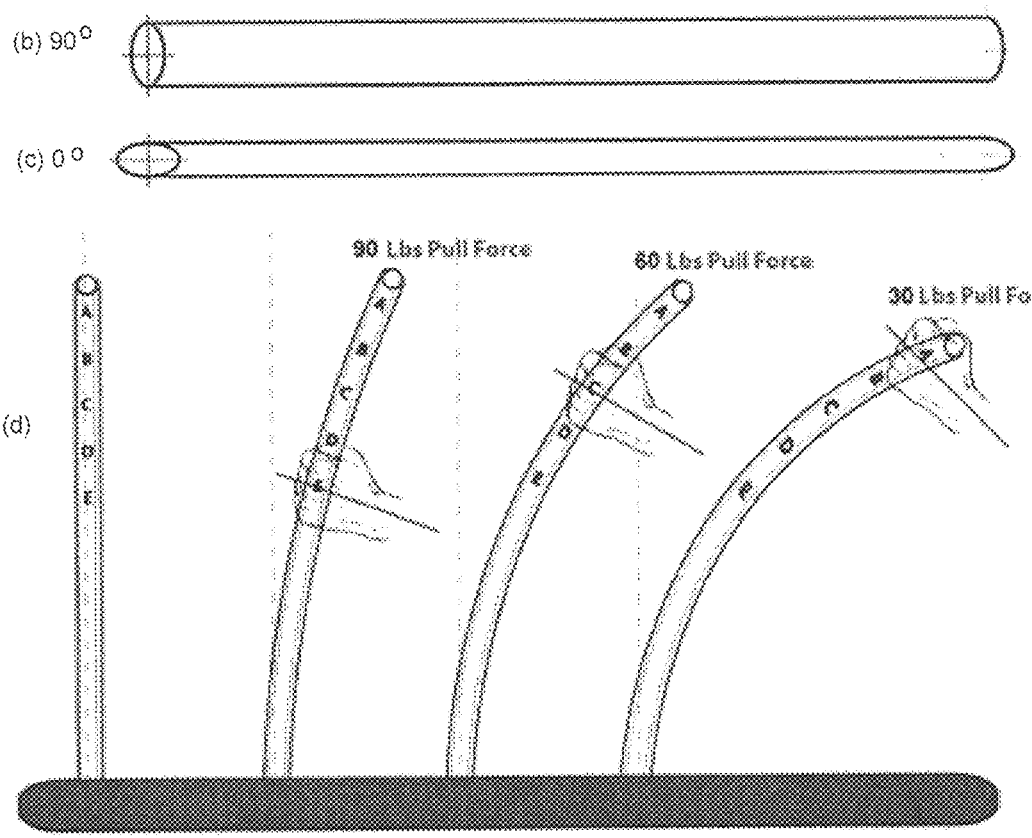

FIG. 1E(a)-(d) illustrates an exemplary embodiment of a type V VRB 100 having a cross-sectional area 125 comprising a major axis longer than a minor axis. That is type V VRB 100 illustrates ellipsoidal beams (hollow or solid) with a major axis longer than minor axis (FIG. 1E(a)). FIG. 1E(b) illustrates a prospective view of VRB 100 with cross-sectional area 120 oriented along the major axis and FIG. 1E(c) illustrates a prospective view of VRB 100 with cross-sectional area oriented such that the major axis is ninety (90) degrees offset from the orientation shown in FIG. 1E(b). FIG. 1E(d) illustrates a series of type V VRB 100 with cross-sectional area 125 demonstrating exemplary bending forces (e.g., 90 Lb, 60 Lb, 30 Lb) for different hand placement. Each new hand position provides a different resistance. Further illustrated is how the resistance increases as fulcrum length decreases, and how resistance decreases as the fulcrum length increases.

Figure 1F:
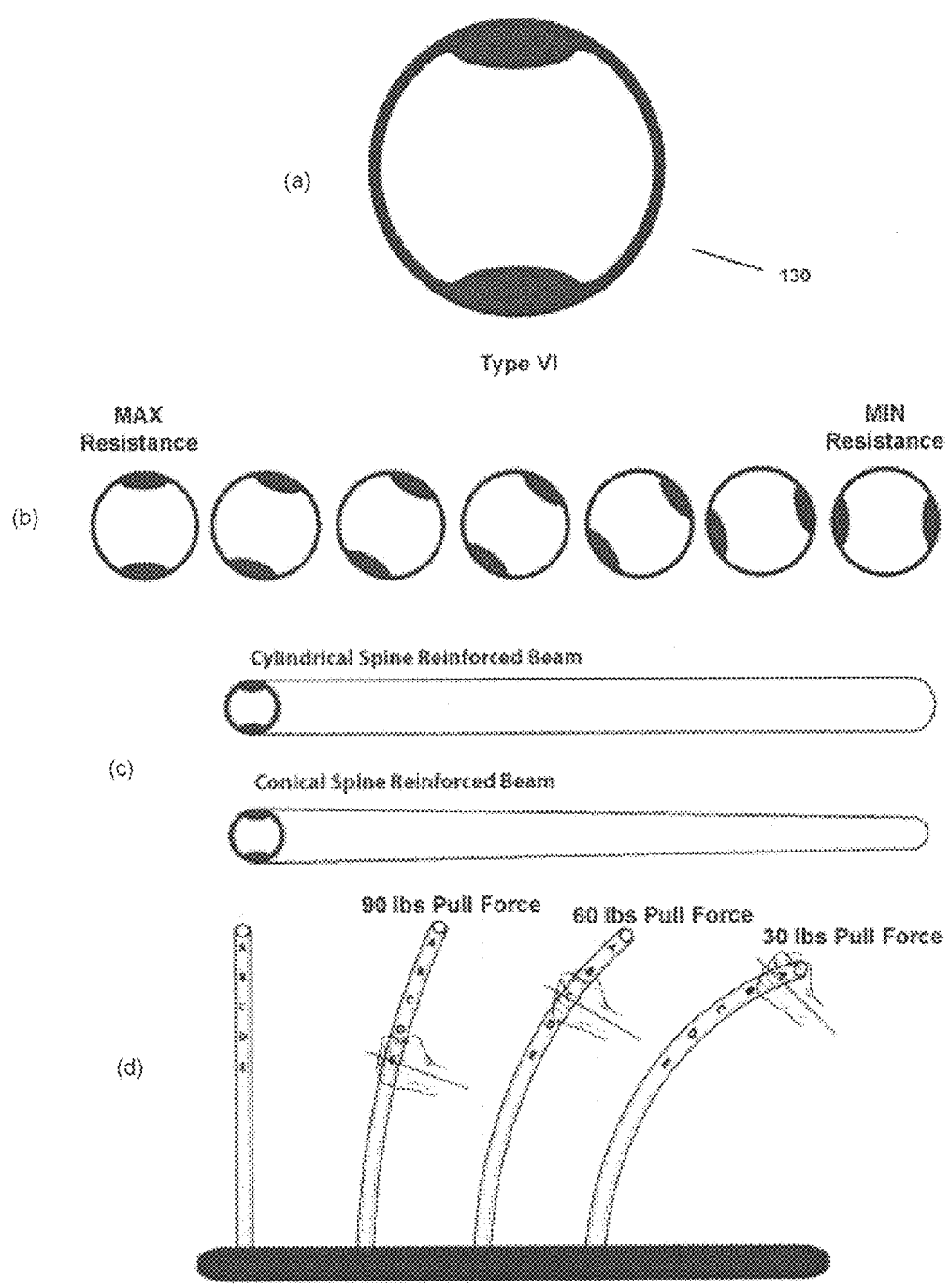

FIG. 1F (a)-(d) illustrates an exemplary embodiment of a type VI VRB 100 having a cross-sectional area 130 comprising a spine reinforced tubular or conical rod (FIG. 1F(a))-FIG. 1F(d) illustrates type VI VRBs 100 with cross-section 130 demonstrating exemplary bending force (e.g., 90 Lb, 60 Lb, 30 Lb) for different hand placement. Each new hand position provides a different resistance. Further illustrated is how the resistance increases as fulcrum length decreases, and in the inverse, how resistance decreases as the fulcrum length increases.

FIG. 1F(b) illustrates change in the resistance of the type VI VRBs 100 as the orientation of the inner splines is rotated with respect to a bending force. In this illustrated example, the resistance to the bending force (not shown) is maximum when the orientation of the inner splines is parallel to the bending force (not shown) and minimum when the orientation of the inner splines is perpendicular to the bending force (now shown).

FIG. 1F(c) further illustrates that the type VI VRBs 100 may also be of a cylindrical or a conical shape.

Figure 1G:
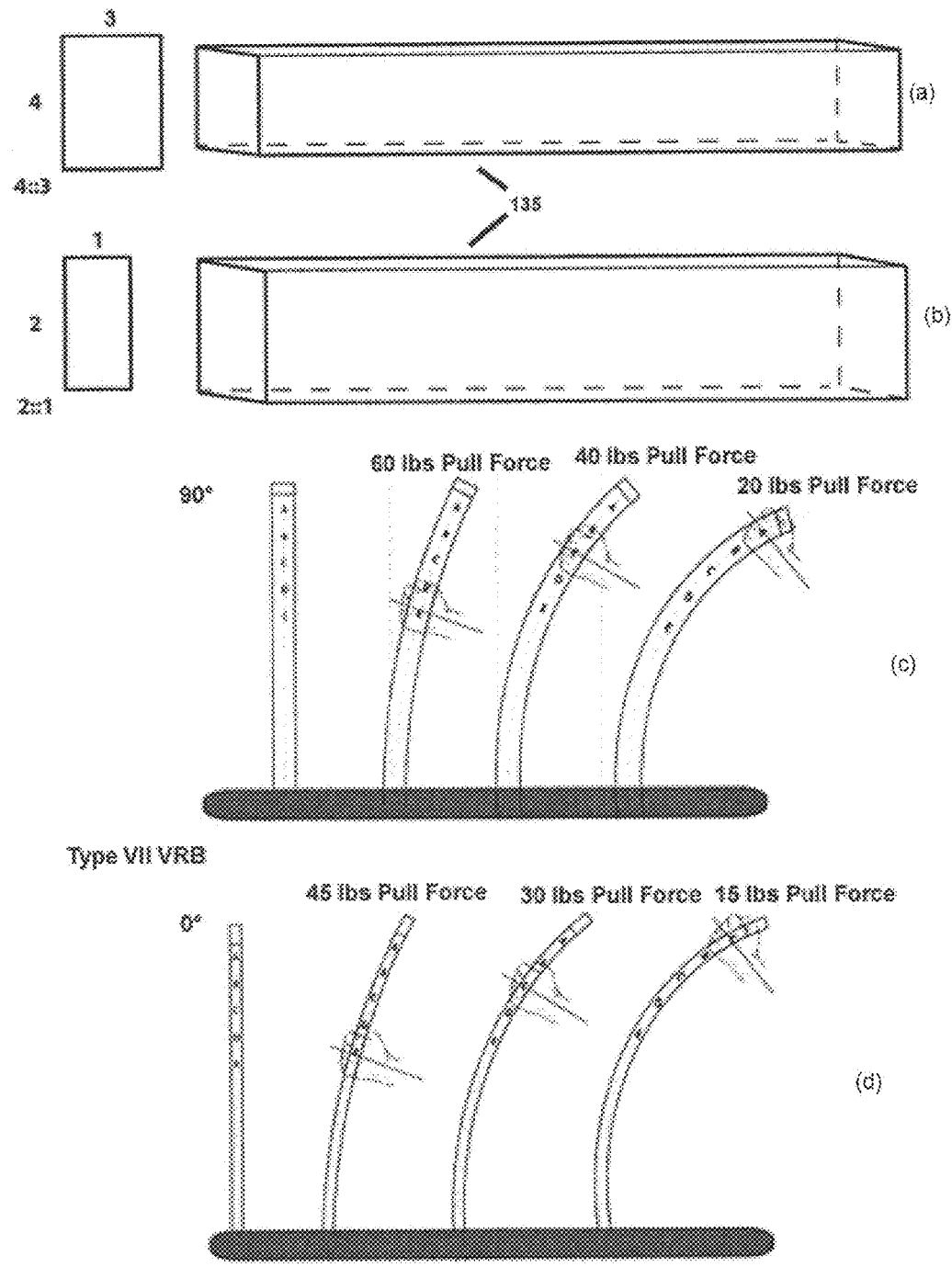

FIG. 1G (a)-(d) illustrates an exemplary embodiment of a type VII VRB 100 beams having a rectangular cross-section 135 (FIG. 1G(a). As shown the rectangular cross-section may be sized in different ratios (e.g., FIG. 1G(a) having a ration of 4:3, and FIG. 1G(b) having a ratio of 2:1) to provide different resistance to bending force. For example, in a case of a 2:1 ratio cross sectional area (FIG. 1G(b), the resistance to a bending force applied to the greater side is twice as great at that of the lesser side. The rectangular type VII VRB 100 may be solid or hollow as desired.

Additionally, the resistance rods (VRBs) may include a plurality of graduated indicia that indicate bending resistance by measurement of a fulcrum distance from an anchored position to a hand position[s], as shown in FIG. 1G(c).

Thus, in one aspect of the invention, rods with symmetrical cross sections vary their bending resistance by shortening and lengthening the arc length, from fulcrum to anchor point by hand position per indicia.

In another aspect of the invention, rods with asymmetrical cross sections may increase or decrease their bending resistance by rotation of the elongated orientation with respect to a bending force, while maintaining the same hand position or fulcrum length FIG. 1G(c) illustrates, for example, different bending forces required (e.g., 60 Lb, 40 Lb, 20 Lb) for different hand positions for a VRB 100 orientation having a larger side of the rectangular cross section parallel to the bending force created by the hand pull while FIG. 1G(d) illustrates different bending forces required (e.g., 45 Lb, 30 Lb, 15 Lb) for different hand positions for a VRB 100 orientation having a large side of the rectangular cross section perpendicular to the bending force created by the hand pull.

Figure 2A:
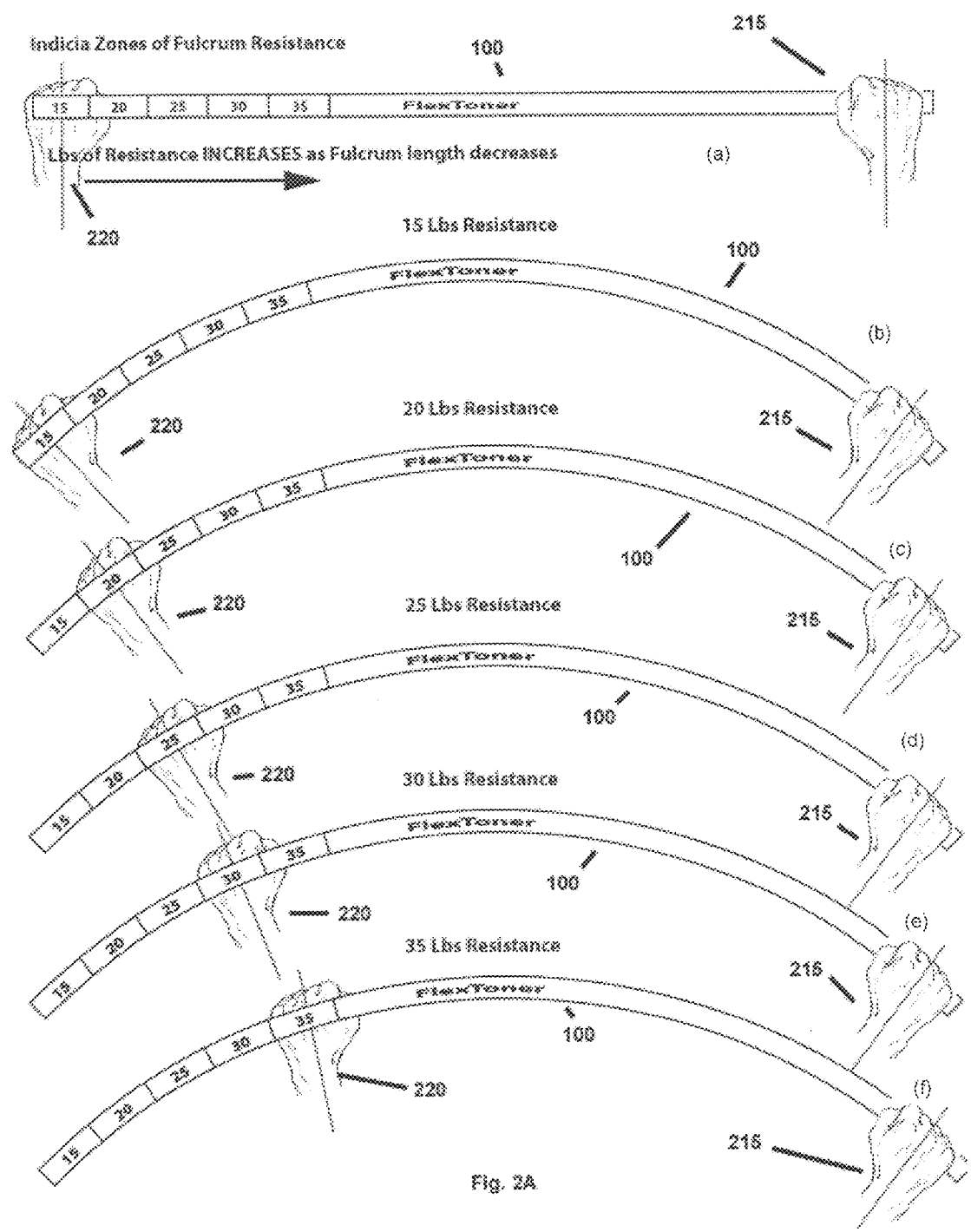

FIG. 2a-2b illustrate the different bending forces for required for various fulcrum changes through hand placement for situations when the VRB 100 is positioned in a minimum resistance position (FIG. 2a) and in a maximum resistance position (FIG. 2b). Each new hand position provides different resistances. VRB 100 illustrates the varies resistances from a cylindrical beam, rod or bar. VRB 100 illustrates the variable resistances from a type II VRB 100 beam, with added geometric spines, indicating, in this instance, the two to-three times increase in pull resistance per identical hand positions along X/Y planes.

Table 1 illustrates exemplary resistance levels for different configurations of the VRBs shown in FIG. 1 and FIG. 4 for a known material. In this case, resistance levels of VRB of 54 inch length, including 6 grip sections, each grip section being 3 inches for 9/16, 5/8 and 3/4 inch nominal VRBs are determined.

As shown in Table 1, the resistance level increases with the addition of a geometric spine in this example. In addition, by shortening or lengthening the arc length/fulcrum during bending of the beam the resistance may be decreased or increased.

TABLE 1

| Distance from fulcrum | 9/16 inch thick bar | | 5/8 inch thick bar | | 3/4 inch thick bar |
|---|---|---|---|---|---|
| | No Spine | With Spine Min/Max Res | No Spine | With Spine Min/Max Res | No Spine |
| 51 | 7 | 8/15 | 10 | 11/21 | 22 |
| 48 | 8 | 8/16 | 11 | 12/23 | 24 |
| 45 | 9 | 9/18 | 13 | 14/25 | 26 |
| 42 | 10 | 10/20 | 14 | 15/28 | 29 |
| 30 | 11 | 11/22 | 16 | 17/32 | 33 |
| 36 | 12 | 13/26 | 18 | 20/37 | 38 |

Also shown, the resistance level increases as the material thickness increases. In addition, the resistance level increases from a minimum to a maximum value as the orientation of the spine with respect to the direction of the flex increases.

Hence, the resistance level that may be achieved at each hand level depends on the thickness of the VRB and the material composing the VRB. Although not shown it would be recognized that the resistance level may further be based on whether the VRB is hollow. With a hollow VRB, the resistance of the VRB depends on a thickness of the outer wall of the VRB.

FIG. 2A(a)-(f) Illustrates a comparison of a symmetric or basically round and an asymmetric or elongated cross sectional VRB 100 rod held at two positions. Further illustrated are indicia indicating different levels of bending force required based ona fulcrum position 215. As illustrated, increasing or decreasing resistance is generated by each rod with a fixed or anchored hand position 215 and a moving hand position 220 into each indicia zone. This distance between fixed hand position and the moving hand position is described as the fulcrum length.

As the fulcrum length or distance between the fixed hand position 215 and the moving hand position 220 increases (see FIG. 2A(f), FIG. 2A(e) through FIG. 2A(a)), the resistance decreases. As the distance between the anchored hand position and the moving hand position decreases, resistance increases (see FIG. 2A(a) through FIG. 2A(f).

FIG. 3(a)-(c) illustrates a VRB 100 with an outside diameter with marked sets of indicia that specify the range of flexural resistances proportionate to the tensile strength of the beam material and fulcrum length per hand position[s] for symmetric or basically round (1 set) and (2 set) asymmetric or elongated cross sections.

FIG. 3(a)-(c) illustrates a side view 300 of an exemplary embodiment of a VRB 100 in accordance with the principles of the invention. FIG. 3(c) illustrates an embodiment of a symmetric VRB 100 including a plurality of hand positions 315, which indicate one set of resistance ranges in relationship to the fulcrum point. FIG. 3(b) illustrates an asymmetric VRB 100, including a plurality of hand positions 310 that indicate two sets or multiple levels of resistance ranges in relationship to the fulcrum point and rotated orientation.

FIG. 4 illustrates a view of an exemplary embodiment 400 of an equipment incorporating a VRB 100 in accordance with the principles of the invention. In this illustrative embodiment, a VRB 100 can be inserted into a plurality of insertion points or rod holders 420. The exercise equipment includes a plurality of tracks 410, a plurality of rod holders 420, a bench 430 that may be positioned substantially perpendicular to the plurality of tracks 410 or at an incline angle with respect to the plurality of tracks.

The tracks may be mechanically fixed in vertical or horizontal planes or any combination to maximize rod bend, defined as mechanical work or exercise matched to human proportion or otherwise described as the ergonomic interface.

FIG. 5 illustrates a view of an exemplary embodiment of an equipment 500 in accordance with the principles of the invention. In this illustrative embodiment, a VRB 100 can be inserted into a plurality of insertion points. The equipment 510 includes at least one track, which can be wall or floor mounted. Each of the at least one tracks includes rod holders 520. In addition, the walls 530 of the rod holder may be perpendicular or conical with respect to the track 510. Rod holders 520 may further include a stabilizing foot 540 in contact with track 510.

The anchored resistance rod (VRB) generates increased or decreased resistance by anchoring the rod at its base and therefore the user can control the degree of rod bend.

This allows the rod to be used as a dynamic resistance beam for useful exercise. The beam resistance is dependent upon the degree of bend and hand position.

FIG. 6 illustrates a view of an exemplary equipment 600 in accordance with the principles of the invention. In this illustrative embodiment, a VRB 100 can be inserted into selected ones of a plurality of insertion points 610 on workout platform 605. In this exemplary embodiment, a plurality of perpendicular rod holders or insertion points 610, similar to those described with regard to FIG. 5, may be incorporated onto a handheld transportable folding workout platform 605.

FIG. 7 illustrates a view of an exemplary equipment 700 in accordance with the principles of the invention. In this illustrative embodiment, there is a VRB 100 held in place by foam or other lightweight material 710 within a hollow shaft 720. The position and/or orientation of the VRB 100 within the hollow shaft 720 may determine the stiffness and/or flexibility of the hollow shaft. That is, in the case, a type I VRB 100 is incorporated into the hollow shaft 720, the length of the type I VRB 100 may determine the stiffness of the hollow shaft. On the other hand, if a type II VRB 100 is incorporated into the hollow shaft, then the orientation of the splines to a proposed bending force determines the stiffness and/or flexibility of the hollow shaft 720.

The resistance beam upon manual customized selected rotation imparts greater flexibility or rigidity to the hockey stick by the user, to customize the equipment's response to the user's athletic ability.

Additionally, another method of imparting greater flexibility or rigidity is to raise or lower the resistance beam within the shaft to change the fulcrum or kick point of the stick.

FIG. 8 illustrates an exemplary embodiment of an equipment 800 in accordance with the principles of the invention. In this illustrative embodiment, an internal VRB 100 is held in position within a hollow shaft by a lightweight material 815, as described with regard to FIG. 7. In addition, one end of the VRB 100 is positioned on a bushing 810 comprising a flexible material such that it may compress or expand as pressure is applied to the bushing 810. In one aspect of the invention, the bushing may be made of an elastometric material such as a polymer, foam, urethane, rubber, or similar material that may be compressed (as represented by the downward pointing arrow) and returned to an original state when the compressive force is removed (as represented by the upward point arrow. At a second end, the VRB 100 is attached to a means 820 for raising or lowering the VRB 100 within the hollow shaft. The means 820 may be a worm gear type mechanism that raises or lowers the VRB 100, to create a variable shaft flex. The VRB 100 may be lowered by compressing the bushing material 810 and raised by removing the compression pressure from the bushing material 810. Although the means for positioning the VRB 100 is shown as a worm gear that may be turned by an Allen key, it would be recognized that other types of rotating means may be incorporated without altering the scope of the invention. For example, the means for adjustment to alter the position of the VRB 100 may be a screw thread position along the outside of the hollow shaft and the turning of a cap on the top of the hollow shaft may lower or raise the VRB 100.

In the illustrated embodiment of the invention shown herein, a VRB 100 rod is centrally raised (wherein the height of bushing 810 is increased) or lowered (wherein the height of bushing 810-is decreased) within the hollow shaft to increase or decrease flexibility or rigidity of the golf shaft, thereby shifting the kick point or maximum point of flexure up or down the hollow section of the shaft. Further illustrated are indicia (i.e., labels 1-5) shown on equipment 800 which indicate a level of compression (or stiffness) or equipment 800.

Thus, the player or user may select a shaft flex or rigidity range that matches the player's specific swing type, strength and ability.

The 360 degree symmetrical geometry provides a solution for an adjustable golf club and would be fully compliant with the existing USGA (United States Golf Association) rules of golf.

FIG. 9 illustrates an exemplary ski sports equipment configuration 900 with an adjustable resistance beam VRB 100 that imparts a resistance range along a length of the body of the ski equipment 900 in accordance with the principles of the invention.

The adjustable resistance beam VRB 100, in this case, 2 VRBs 100 positioned along longitudinal edges of both pairs of skis comprising ski equipment 900 imparts a range of performance characteristics into the ski equipment 900 to match the skier's skill and terrain requirements.

In one application of the VRB 100 described herein, downhill skiing requires a very rigid ski. By adjusting the resistance beam to the highest rigidity setting, the ski equipment 900 will become more rigid with a faster dynamic response when carving turns. A more rigid ski equipment is desirable for icy conditions due to the ability to hold its shape and maintain maximum edge contact with the snow and ice surface.

In another application, mogul skiing over bumps requires a flexible ski equipment. By adjusting the resistance beam to its most flexible setting, the ski equipment 900 will become more conformal to bumps and bend and flex over them.

Thus a terrain adaptable ski is created from a mechanically joined adjustable resistance beam.

The means for positioning the VRB 100 within ski equipment 900 may be similar to that described with regard to FIG. 8.

FIG. 10A illustrates a view of an exemplary embodiment of a lawn equipment 1000 in accordance with the principles of the invention. In this illustrative embodiment, tines are individual VRBs 100, and can be simultaneously adjusted to create equal flex in each tine.

FIG. 10B illustrates a bottom view of an exemplary embodiment of a lawn equipment 1000 in accordance with the principles of the invention. In this illustrative embodiment, the tines VRB 100 may be simultaneously rotated equally to create variable flex.

The rotated tines are locked into an incremental range of resistance positions that are either the most flexible for raking leaves or the most rigid to raking gravel. At the end of each tine is an ellipse that acts a hook dependent upon its rotated orientation.

FIG. 11 illustrates a view of an exemplary embodiment of an equipment 1100 in accordance with the principles of the invention. In this illustrative embodiment, internal VRBs 100 are adjusted to create a variable flex. Equipment 1100, which represents an athletic shoe, includes a rubber shoe sole 1115. The athletic shoe 1100 further includes a heel fulcrum 1125 and a toe fulcrum 1130. Between the heel fulcrum 1125 and the toe fulcrum 1130 is an internal cavity 1110. Within cavity 1110 is positioned at least one VRB 100. The VRB 100 includes anti-rollover collars 1110*a*, which prevent the VRB beam deflection or distortion and are spaced along the VRB 100. The at least one VRB 100 located within the internal cavity 1110 may be adjusted by an adjustment means 1120 that rotates the VRB within cavity 1110. The VRB 100 is further locked in position. The means for positioning the VRB may be similar to that described with regard to FIG. 8.

The transmission of the shoe wearer's strength (power) from their legs into the ground is directly affected by the sole stiffness of the shoe. By employing an adjustable resistance beam as described herein, runners may gain more leverage and, thus more speed, by using a responsive shoe sole customized to their specific requirements.

An adjustable pair of resistance beams within the shoe sole may be insertable, insert molded or structurally connected to the shoe sole in lateral and/or longitudinal positions within the sole and are rotatable to a fixed and mechanically locked position to effect custom flexural resistance range that matches the wearer's optimum performance requirement.

Thus, the resistance beam technology described herein is designed to be a dynamic, adjustable, in-sole suspension system that can absorb the weight of the wearer and release it per each step.

FIG. 12 illustrates an exemplary medical brace in accordance with the principles of the invention. In this illustrative example, at least one VRB 100 is incorporated into a VRB assembly 1215 into an anchor 1230, an adjuster 1220, and a fulcrum 1210. The bracing system in FIG. 12 is comprised of a thigh leg strap collar 1205 attached to a frame with a fulcrum 1210 connected to a hinge 1225 with an upper arm 1240 with a bushing piston acting as a second cartilage.

In this illustrative embodiment, VRBs 100 are adjusted to create a variable flex. Element 1205 illustrates leg strap or collar (thigh) strap. Element 1205*a* illustrates leg strap or collar (calf) strap. Element 1210 illustrates fulcrum for VRB to maintain controlled bending. Element 1215 illustrates a VRB assembly (one or more VRB's) that acts as a leaf-spring/unloader; i.e., a first suspension point. Element 1220 illustrates VRB assembly adjuster to customize flexibility or resistance. The assembly adjuster 1220 may be a worm gear as previously described. Element 1225 illustrates a hinge that mimics the bio-mechanical movement or range of an anatomical joint (e.g. knee). Element 1230 illustrates VRB assembly anchor with spring/bushings: i.e., a secondary suspension point. Element 1240 illustrates a telescoping upper hinge arm with a bushing piston, a second cartilage: i.e., a third dampening or cushioning point. VRB assemblies 100*a* or 1215 provides a dynamic supportive structure designed to act as an artificial or second knee to support a damaged or injured one.

An additional benefit of incorporating the VRB 100 technology into medical devices is that the resistance rods, under compression, create a proportioned constant vertical lift to unload 115 and dynamically support the joint (e.g., a knee) during post op, rehabilitation, arthritis or during extreme sports. Hence, the VRB 100 technology described herein provides a truly functional and adjustable brace that provides for Shock Absorbing, Active Suspension, Adjustable Comfort DST Unloader Knee Brace.

A VRB 100, which may be solid, semi-hollow or hollow, with or without geometrically created I-beam effect (i.e., Asymmetric geometry, spines) on the outside or interior diameter generates resistance depending on the axis of orientation and/or a fulcrum position has been described herein. A VRB 100, with incorporated I-beam geometry on the outside diameter, may allow for the dynamic adjustment of resistance of the device. An advantage of a device including a VRB's described herein, may be compact, lightweight and offer the ability to more easily and quickly change a desired level of resistance than is typically found in units using weights, rubber bands, bows or springs. By simple reposition or rotation of a VRB incorporated into the device, a desired selectable range of resistance level may be achieved. The VRB's 100 disclosed, herein, can provide resistance, depending on the orientation of the beam, to a bending direction. In addition, an exemplary device incorporating the VRB technology may vary the resistance provided to the user during rehabilitative exercise, without interrupting the exercise cycle. Additional beam resistance is achieved depending upon the relative orientation of the beam within a 180° degree hemisphere of movement relative to the user.

Hence, according to the principles of the invention, a progressive dynamic resistance may be achieved with a variation of the orientation of the beam or shaft shown herein.

In one aspect of the invention, rods with symmetrical cross sections vary their bending resistance by shortening and lengthening the arc length, from fulcrum to anchor point by hand position per indicia.

In another aspect of the invention, rods with asymmetrical cross sections may increase or decrease their bending resistance by rotation of the elongated orientation with respect to a bending force, while maintaining the same hand adjusted position or fulcrum length.

In one aspect of the invention, the VRB's 100 may be composed of thermoplastic polymers, especially high tenacity polymers, include the polyamide resins such as nylon; polyolefin, such as polyethylene, polypropylene, as well as their copolymers, such as ethylene-propylene; polyesters, such as polyethylene terephthalate and the like; vinyl chloride polymers and the like, and polycarbonate resins, and other engineering thermoplastics such as ABS class or any composites using these resins or polymers. The thermoset resins include acrylic polymers, resole resins, epoxy polymers and the like.

Polymeric or composite materials may contain reinforcements that enhance the stiffness or flexure of the flexure resistance spine. Some reinforcements include fibers, such as fiberglass, metal, polymeric fibers, graphite fibers, carbon fibers, boron fibers and Nano-composite additives, e.g. carbon nano-tubes, et al, to fill the molecular gaps, therefore strengthening the material.

Additional materials that the resistance rods or VRB's may also be composed of include high tensile aircraft aluminum and high carbon spring steel and/or high tensile strength to weight materials.

FIG. 13A illustrates a perspective view of an exemplary brace assembly 1300, in the form of a knee brace, encompassing knee 1303, in accordance with the principles of the invention.

Brace 1300 comprises an upper frame 1307 comprising an upper collar 1305 and upper collar strap 1305a that encircles the thigh and connects to upper collar 1305. Collar strap 1305a may be attached to upper collar 1305 using a belt attachment or VELCO, for example. VELCO is a registered trademark of VELCO IndustriesBV LLC Netherlands. Brace 1300 further comprises a lower frame 1309 comprising a lower collar 1306 and lower collar strap 1306a. In this illustrated example, the lower collar strap 1306a extends from a first side to a second side of lower collar 1306 along the shin. Collar strap 206a attaches to collar 1306 using VELCO, for example.

Upper frame 1307 further includes extensions 1307a that extend downward from the upper collar 1305. Lower frame 1309 similarly includes extensions 1308a that extend upward from lower collar 1309. Although not shown, it would be appreciated that brace 1300 includes two such extensions 1307a and 1308a; one on either side of knee 1303. Extensions 1307a and 1308a represent attachment means that enable upper frame 1307 and lower frame 1309 to interact with one another.

A rotatable hinge 1310, connected to the extensions 1307a and 1308a, joins the upper frame arm 1307 and the lower frame arm 1309, to allow rotation of the upper frame 1307 with respect to the lower frame 1309. Hinge 1310 allows the contained joint (i.e., a knee 1303) to bend and flex in a conventional manner. In one aspect of the invention, hinge 1310 may be locked to retain a fixed orientation of the upper frame 1307 with respect to the lower frame 1309.

In this illustrated embodiment, a compression assembly 1320 is incorporated into each of extension arms 1307a or 1308a. Compression assembly 1320 comprises an arm 1325 extending from hinge 1310, which is slidably engageable with a piston type assembly compression mechanism 1327. Compression mechanism 1327 includes an adjustable VRB and bushing, as will be discussed.

Arm 1325 transmits vertical load into the compression mechanism 1327, which is counterbalanced by the VRB resistance setting. The VRB acts as a cantilever providing reactive and dynamic suspension. The VRB, thus, provides prescriptive settings to lift or separate the patella-femoral knee joint incrementally, to minimize injury and maximize rehabilitative support and recovery.

FIG. 13B illustrates a side view of a polycyclic gear assembly in accordance with the principles of the invention.

In this illustrative example, extensions 1307a and 1308a engages gear 1310 from upper and lower directions, as previously described. Incorporated in extension 1308a is compression assembly 1320. Arm 1325 slidably engages compression mechanism 1327. Compression mechanism 1327 includes VRB 100 and an elastomer material bushing 1330. The elastomer material bushing 1330 is positioned opposite a free end of arm 1325 and VRB 100 is positioned between bushing 1330 and free end of arm 1325. VRB 100 and elastomer material 1330 provide a resistive force to counterbalance vertical load through the polycyclic gear 1310.

FIG. 14A-FIG. 14C illustrate exemplary examples of compression means 1320, shown in FIG. 13A in different configurations of rigidity, in accordance with the principles of the invention.

FIG. 14A(a) illustrated a front view and FIG. 14A(b) illustrates a side view of compression assembly 1320 in a maximum rigidity state. In this illustrated example, hinge 1310 is shown positioned in a substantially vertical orientation. However, it would be recognized that hinge 1310 is bendable about a focal point 1405.

Referring to FIG. 14A(a), in this illustrated embodiment, upper frame arm 1307a includes a rounded lower end 1403 that is pivotable about a bearing 1404. Similarly, lower frame arm 1308a (not shown) includes a rounded upper end 1406 that is pivotable about bearing 1404. Focal point 1405 is determined as the point between rounded lower end 1403 and rounded upper end 1406 and is the point that hinge 1310 rotates about.

Compression assembly 1320 is attached to bearing 1404 (hinge 1310) on a first end and to lower frame arm 1308a (now shown) at a second end, in this illustrated case. Compression assembly 1320 comprises an elastomer bushing 1330 and a variable resistance beam VRB 100. VRB 100 extends at an angle offset from a perpendicular to bushing 1330.

Further illustrated is bushing element 1330 having a convex upper surface and a concave lower surface. VRB 100 is positioned on the upper surface of bushing 1330, which enables VRB 100 to flex or bend as vertical loads are absorbed between the upper frame 1307 to the lower frame 1309.

The shape of bushing 1330 further provides a shock absorbing back up and/or redundant cushioning system when the mechanical capacity of VRB 100 to absorb a downward load exceeds its mechanical ability to resist the load. In another aspect of the invention, bushing element 1330 may be principally a rectangular block in shape.

In this illustrated example, VRB 100 is positioned or oriented to achieve a maximum rigidity in absorbing loads transferred from the upper frame 1307 to the lower frame 1309 by VRB 100 being oriented in a maximum rigidity position. FIG. 14A(b) illustrates a cross-sectional view, wherein VRB 100 has an orientation having a largest diameter, and hence, a maximum degree of rigidity. The maximum force of VRB setting provides the highest patella-femoral LIFT/Separation and Dynamic (Load) Suspension for the knee.

FIG. 14B(a) illustrates a front view and FIG. 14B(b) illustrates a side view of another configuration of compression assembly 1320. As FIG. 14B is comparable to FIG. 14A, a description of those elements described in FIG. 14A that are similar to those elements shown in FIG. 14B need not be repeated.

As shown in FIG. 14B(a), VRB 100 is positioned in a middle resistance position. In this case, compression assembly 1320 provides a medium (or mid-level) degree of rigidity to bending of VRB 100 as vertical loads are transferred from the upper frame 1307 to the lower frame 1309. FIG. 14B(b) illustrates a cross-sectional view, wherein VRB 100 has an orientation of a mid-level resistance, and hence, a mid-level degree of rigidity.

The middle force of VRB 100 setting provides for medium patella-femoral lift and/or Separation and Dynamic (Load) Suspension for the knee.

FIG. 14C(a) illustrates a front view and FIG. 14C(b) illustrates a side view of still another configuration of compression assembly 1310. As FIG. 14C is comparable to FIG. 14A, a description of those elements described in FIG. 14A and similar to those elements shown in FIG. 14C need not be repeated.

FIG. 14C(a) illustrates an example wherein VRB 100 is positioned in a minimum resistance mode. In this illustrative example, VRB 100 provides a minimum degree of rigidity to bending as loads are transferred from the upper frame 1307 to the lower frame 1309. FIG. 14C(b) illustrates a cross-sectional view, wherein VRB 100 has an orientation of a minimum diameter, and hence, a minimum degree of rigidity.

The minimum force or VRB setting provides the minimum patella-femoral lift and Separation and Dynamic (load) Suspension for knee.

A comparison of FIGS. 14A(b), 14B(b) and 14C(b) reveals that a diameter of VRB 100 traverses from a maximum diameter(maximum rigidity) to a minimum diameter (minimum rigidity) to change the degree of rigidity.

Figure 15A:
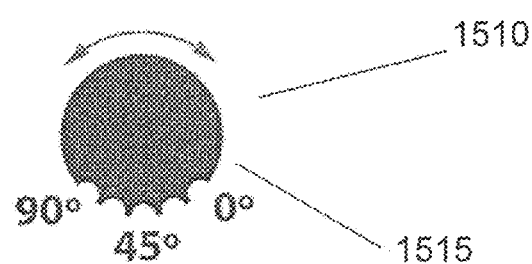

FIG. 15A illustrates a cross-section view of an exemplary configuration 1510 of a head of VRB 100 that operates with a worm gear assembly in accordance with the principles of the invention.

In this illustrative configuration, VRB 100 (not shown) includes a substantially circular head 1510 including gear 1515 that, as will be discussed, allows VRB 100 to rotate from a minimum resistance position to a maximum resistance position, as will be described.

That is, VRB 100 rotates from a minimum resistance position corresponding to a minimum diameter (0°) to a maximum resistance position corresponding to a maximum diameter (90°).

However, it would be appreciated that the terms "minimum resistance" and "maximum resistance," as used herein may similarly correspond to a maximum and minimum fixed rotation positions, without altering the scope of the invention. That is, the application of VRB 100 determines whether a minimum resistance position corresponds to a minimum resistance (or rigidity) or to a maximum resistance (or rigidity).

While the exemplary VRB head 1510 is shown containing geared portion 1515 along a partial circumference of VRB head 1510, it would be recognized that geared portion 1515 may extend around the entire circumference of VRB head 1510. In such a configuration, the VRB 100 may rotate from a minimum resistance to maximum resistance and back to a minimum resistance as VRB 100 continues to rotate in a same direction.

Figure 15B:
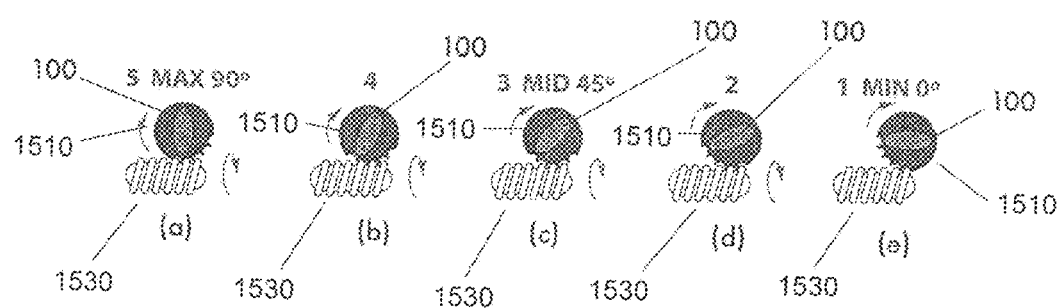

FIG. 15B (comprising FIGS. 15B(a) through 15(e)) illustrates an exemplary rotation of VRB 100 as worm gear 1530 is rotated against geared VRB head 1510 including gear 1515. Also illustrated is the orientation of VRB 100. In this case, VRB 100, which is illustrated as having an elliptical cross-section, is rotated from a maximum resistance position (FIG. 15B(a)) to a minimum resistance position (FIG. 15B(e)). Although VRB 100 is shown as being of a substantially elliptical shape, it would be recognized that any one of the VRBs cross-sectional view shown in FIG. 1(b)-FIG. 1(g) may be utilized without altering the scope of the invention.

Figure 15C:
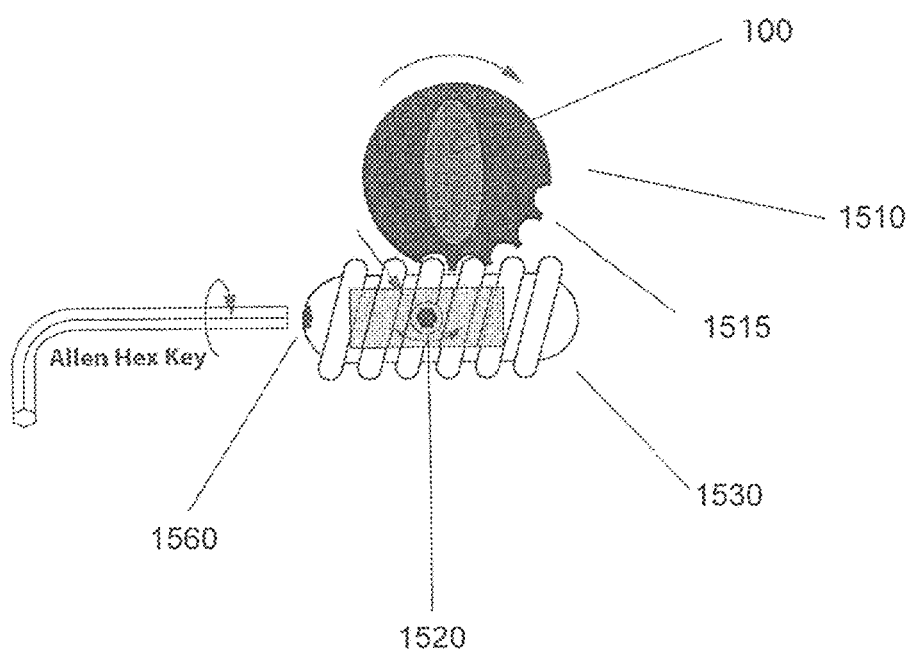

FIG. 15C illustrates an enlarged view of worm gear 1530 showing the engagement with gear 1515 of head 1510 of VRB 100. Worm gear 1530 may include an adjustment means such as an indentation 1560, which captures an Allen key or Torx key, for example, that rotates worm gear 1530.

As worm gear 1530 rotates, the rotation of worm gear 1530 is transferred to the gear 1515 of head 1510 such that VRB 100 may rotate, as shown in FIG. 15B.

FIG. 15C further illustrates a locking plate 1520. Locking plate 1520 retains worm gear 1530 (and consequentially VRB 100) in a locked position.

Figure 15D:
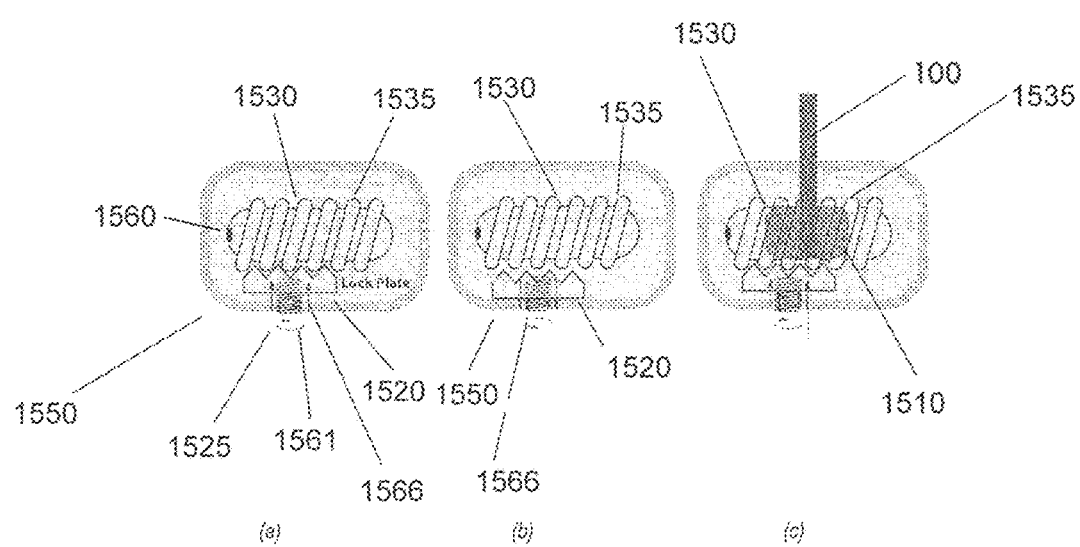

FIG. 15D (comprising FIGS. 15D(a)-15D(c)) illustrates a top view of worm gear assembly 1550 including worm gear 1530 and locking plate 1520. Further illustrated is screw (e.g. a set screw) 1525 that alters the position of locking plate 1520 with respect to worm gear 1530.

In one aspect of the invention, as shown in FIG. 15D(a), assembly 1550 includes a threaded opening 1561, through which passes set screw 1525 to engage locking plate 1520. As set screw 1525 is rotated in a first direction, locking plate 1520 is moved toward worm gear 1530. Locking plate 1520 further includes a toothed surface opposite screw threads 1535 of worm gear 1530. As locking plate 1520 advances towards worm gear 1530, the toothed surface of plate 1520 engages the screw threads 1535 of worm gear 1530. In this position, worm gear 1530 is locked in position. Thus, the position of the VRB 100 is fixed at that position to which VRB 100 has been rotated by the rotation of worm gear 1530.

In another aspect of the invention, FIG. 15D(b), screw 1525 is rotated in a opposite direction, causing the toothed surface of locking plate 1520 to withdraw from screw threads 1535 of worm gear 1530. In this illustrative embodiment, worm gear 1530 is free to rotate.

As would be appreciated, a screw hole 1566 and locking plate 1520 are aligned with threaded screw hole 1565, through which screw 1525 is captured to locking plate 1520. In this manner, locking plate 1520 moves inward or outward along screw 1525 as screw 1525 is rotated. Screw hole 1566 allows alteration of the position of locking plate 1520 by an adjusting mechanism, such as an Allen Key, to rotate screw 1525.

FIG. 15D(c) illustrates a top view of exemplary embodiment of the worm gear assembly 1550 in accordance with the principles of the invention. In this exemplary embodiment, locking plate 1520 engages screw threads 1535 of worm gear 1530. Also illustrated is VRB head 100 that engages screw threads 1535 (through gear 1515, not shown).

As previously discussed, rotation of worm gear 1530 causes rotation of head 1510, through engagement of gear 1515, which in turn causes rotation of VRB 100. In this exemplary embodiment, plate 1520 engages the screw thread 1535 to prevent altering the position of VRB 100, as shown with regard to FIG. 15D(a). Thus, the orientation of VRB 100 is fixed.

FIG. 16A illustrates a front view and FIG. 16B illustrates a side view of compression assembly 1320.

Referring to FIG. 16A, compression assembly 1320 comprises an arm 1325 that slidably engages compression mechanism 1327 within housing 1328. Also shown is VRB 100 and elastomer bushing 1330. VRB 100 is rotated, as previously discussed, from a minimum rigidity position to a maximum rigidity position through gear 1530.

As previously discussed, as the orientation of VRB 100 is altered from a minimum diameter to a maximum diameter with respect to bushing 1330, the rigidity of VRB 100 in absorbing loads varies from a minimum to a maximum.

The positioning of VRB 100 creates a separation between bushing 1330 and a lower end of arm 1325. The separation varies as the orientation of VRB 100 changes from a minimum diameter position to a maximum diameter position (see FIGS. 14A-14C).

Also shown is indicia or marking (numbers 1-5) on a surface of housing 1328. The indicia or markings provide an indication of the degree of rigidity of VRB 100.

FIG. 16B illustrates a side view of compression assembly 1320. In this illustrated case, thread 1535 of gear 1530 are shown engaging gear 1515 of VRB head 1510.

Further illustrated is an Allen Key that may be used to engage indentation 1560 to turn gear 1530.

FIG. 17 illustrates an expanded view of compression mechanism 1327 in accordance with the principles of the invention.

In this illustrative example, compression mechanism 1327 includes VRB 100 oriented substantially perpendicular to elastomer material 1330. Gear 1530, as previously discussed, when turned changes the orientation of VRB 100 from a minimum rigidity position to a maximum rigidity position with respect to elastomer material 1330.

Also shown is set screw 1525 that alters the position of locking plate 1520. As previously discussed, the position of locking plate 1520 determines whether gear 1530 is either free to rotate or retained in a fixed position.

FIG. 18A-FIG. 18B illustrate a second embodiment of the incorporation of a compression assembly 1320 in accordance with the principles of the invention. In this illustrative example, compression assembly 1320 is incorporated into upper attachment mechanism 1307a.

FIG. 18A illustrates a condition where a maximum rigidity position is obtained and FIG. 18B illustrates a condition wherein a minimum rigidity position is obtained. VRB 100 and bushing 1330 are not illustrated. However, it would be understood that bushing 1330 is opposite the unattached end of arm 1325 and VRB 100 is positioned between bushing 1330 and the unattached end of arm 1325.

FIG. 19A-FIG. 19E illustrate a second exemplary configuration for controlling rotation of a VRB utilized in the knee brace shown in FIG. 13A.

Figure 19A:
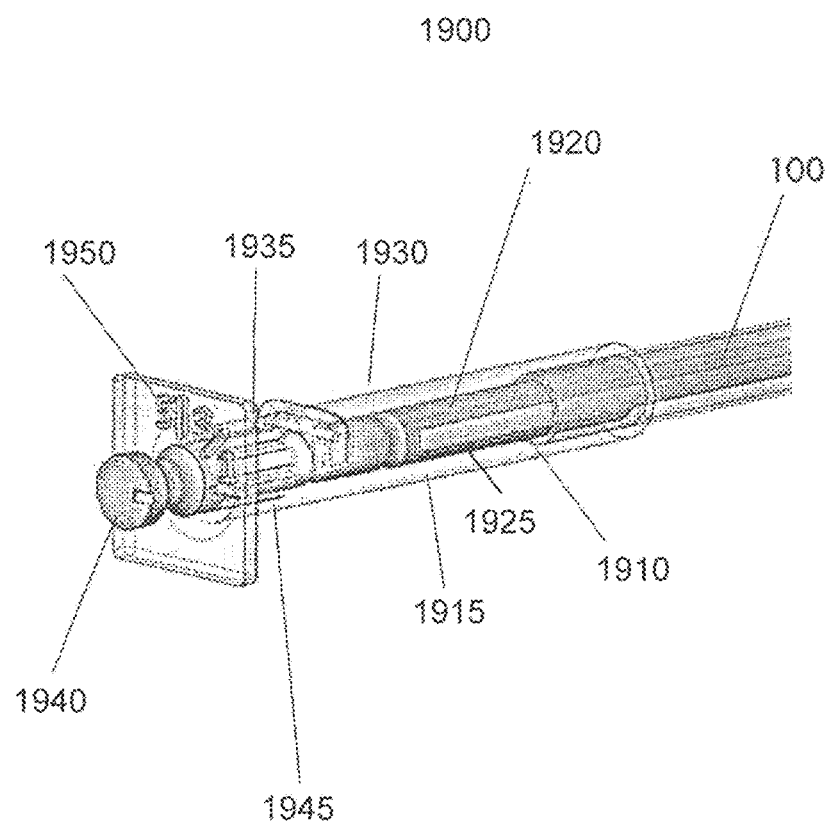

FIG. 19A illustrates a perspective view 1900 of a second exemplary configuration of a control means 1900 in accordance with the principles of the invention.

In this exemplary configuration, referred to herein after as "spline/socket", which represents a manual, geared mechanism that selectively rotates a VRB (variable resistance beam) in controlled increments ranging from 0° to 90° while simultaneously controlling torque.

In this illustrated example, the spline/socket mechanical arrangement creates a secure, adjustable anchor point to prevent VRB 100 rotation.

As shown, the socket/spline 1900 provides an adjustable locking system that secures a VRB 100 from rotation and therefore mechanically maintains a constant resistance or suspension.

As shown, VRB 100, which has been previously described includes a maximum diameter and a minimum diameter. VRB 100 further includes a fork or tongue 1910 that is insertable into spline 1920. Spline 1920 is a substantially round, solid, rod including tongue or fork 1925. Tongue or fork 1925 engages (and matches) tongue or fork 1910 of VRB 100.

Also shown is socket 1930 into which spline 1920 is inserted. Socket 1930 contains fork 1925 and tongue 1910 in a manner such that as spline 1920 is rotated, VRB 100 similarly rotated.

At a proximal end of socket 1930 is shown grooves 1935 and spline elements 1945 formed between adjacent ones of grooves 1935. In one aspect of the invention, the spacing of spline elements 1945 (grooves 1935), provides for a desired degree of locking rotation. For example, 16 spline elements 1945 provide for 22.5° of incremental VRB rotation. (360°/16=22.5°).

In accordance with the principles of the invention, the VRB 100 plus spline 1920 form an adjustable assembly, wherein the spline 1920 maybe pulled out by grasping spline head 1940, rotating the spline 1920 and re-inserting the spline 1920 into socket 1930, to provide a higher or lower resistance or suspension level. This level of resistance is dependent upon the locked rotation angle of the VRB.

Also illustrated is faceplate 1950. Faceplate 1950 presents an indicia of the degree of turning of VRB 100.

As would be appreciated, tongues or forks 1925 and 1910 are sized so that they are always engaged, even when spline 1920 is pulled out, turned and re-inserted into socket 1930.

Figure 19B:
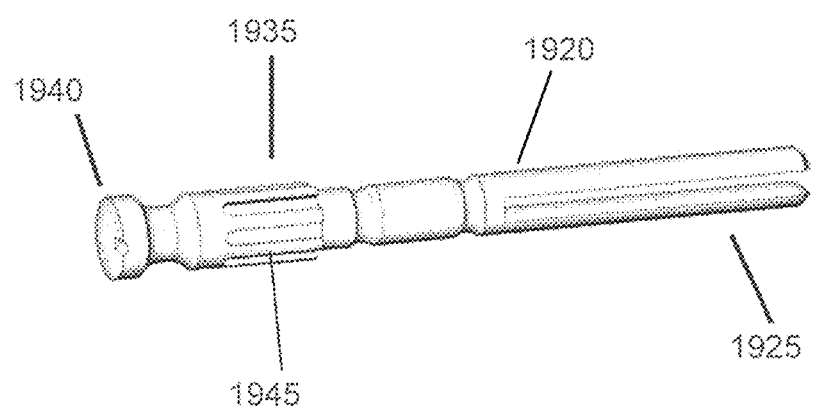

FIG. 19B illustrates a perspective view of spline 1920. In this illustrative embodiment, spline 1920 is a substantially cylindrical rod including at a first end fork 1925 and a spline head 1940 on a second end. Further illustrated are spline elements 1945 positioned about the circumference of spline 1920 between adjacent ones of grooves 1935.

As shown a length of fork 1925 is sufficiently greater than a length of spline elements 1945 in order to prevent spline 1920 from disengaging VRB 100 (not shown) when spline 1920 is pulled from socket 1930

Figure 19C:
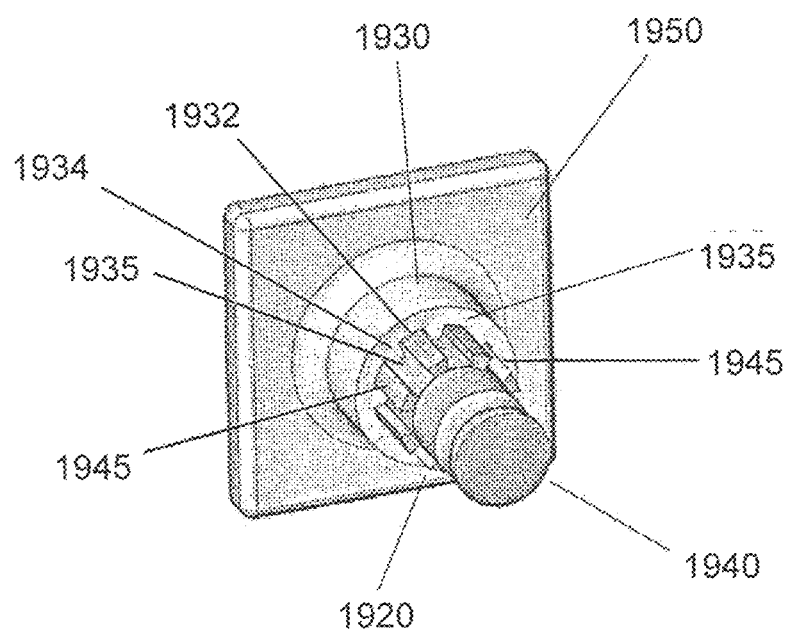

FIG. 19C illustrates a perspective view of a spline element 1945 of spline 1920 engaging grooves 1932 of socket 1930. In this illustrative example, socket 1930 includes a plurality of grooves 1932 and spline elements 1934 between adjacent ones of grooves 1932. Grooves 1932 and spline element 1934 of socket 1930 match in number and width, grooves 1935 and spline elements 1945 of spline 1920.

As discussed, spline 1920 may be withdrawn from socket 1930, rotated and reinserted into socket 1930. The rotated and reinserted spline 1920 alters the position of the VRB 100 (not shown) such that a different level of rigidity of VRB 100 is achieved (see FIG. 14A-FIG. 14C). The engagement of spline elements 1945 with grooves 1932 lock and retain VRB 100 (not shown) in a desired position.

Figure 19D:
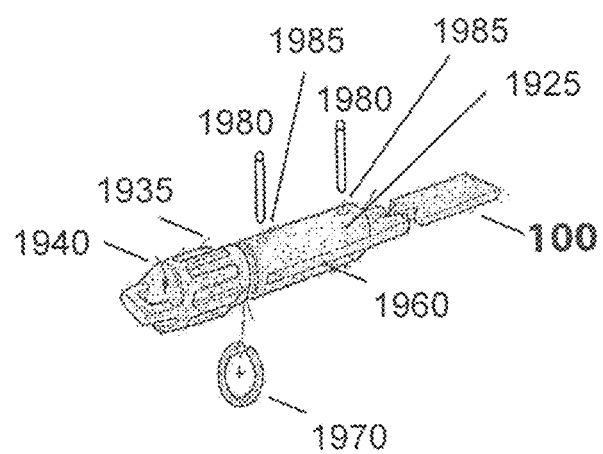

FIG. 19D illustrates a perspective view of a control mechanism 1900 illustrating VRB 100 engaging fork 1925 in spline 1920 in accordance with the principles of the invention.

In this illustrative embodiment, VRB 100, which is shown having a rectangular cross-section, includes tongue 1910 that may be inserting into fork 1925 in order to provide a secure connection between tongue 1910 and fork 1925, as previously discussed.

Further illustrated is retaining ring 1970. Retaining ring 1970 represents a spring loaded mechanism that enables spline head 1940 to be withdrawn from socket 1930 by pushing spline head 1940 into socket 1930. The act of pushing spline head 1940 into socket 1930 disengages retaining ring 1970 and the spring loaded mechanism forces spline head 1940 to withdraw from socket 1930. In one aspect of the invention, retaining ring 1970 may be constructed of a springable material and shaped to operate as spring mechanism.

Further illustrated are pins 1980, which when inserted into holes 1985 provide a secure connection between fork 1925 and tongue 1910.

As would be appreciated holes 1985 may be elongated in order to allow spline head 1940 to be withdrawn a limited distance from socket 1930. Hence, spline head 1940 may not be totally withdrawn from socket 1930 even if spline head 1940 is inadvertently pushed in.

Figure 19E:
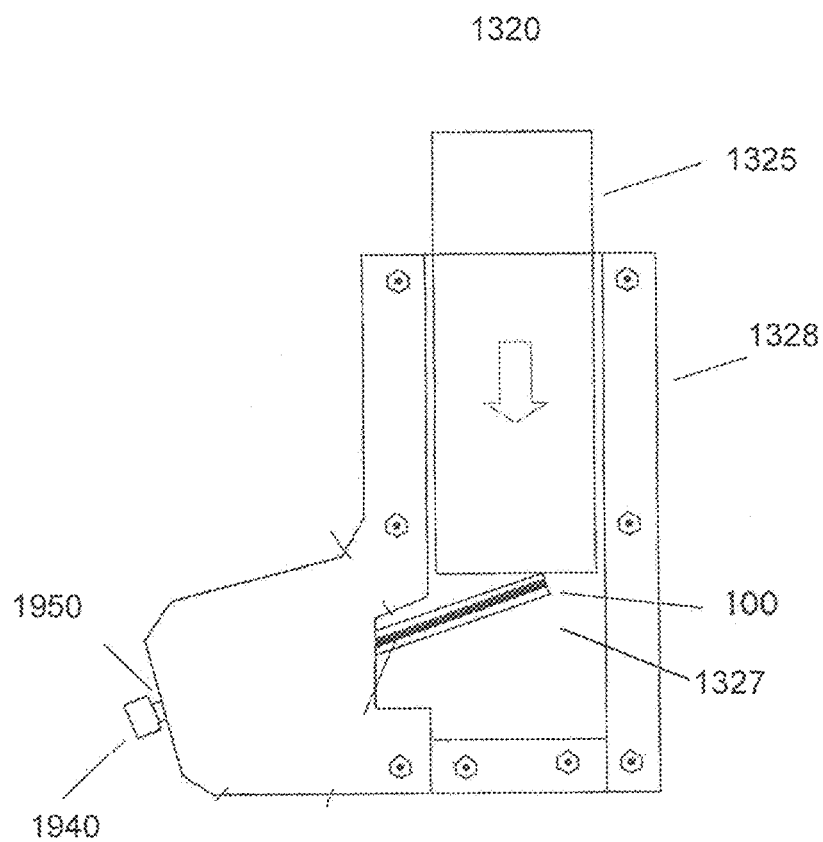

FIG. 19E illustrates a cross-sectional view of compression mechanism 1320 in accordance with the secondary exemplary adjustment mechanism in accordance with the principles of the invention.

As shown, compression assembly 1320 comprises an arm 1325 that slidably engages a housing 1328. Also shown is VRB 100, which is one element of compression mechanism 1327, engaging a lower face of arm 1325. Bushing 1330 is not shown.

VRB 100 is rotated, in this exemplary embodiment, using a spline/socket mechanism shown in FIGS. 19A-19D, from a minimum rigidity position to a maximum rigidity position, as previously described. However, it would be appreciated that the worm gear mechanism illustrated in FIG. 15 may also be utilized without altering the scope of the invention.

Hence, in accordance with the principles of the invention, the VRB Cantilever piston compression assembly 1320 illustrated mechanically acts as a piston arm that separates the upper arm 1325 from the lower brace assembly 1309 (see FIG. 13A).

Arm 1325 rides on top of the VRB 100 to transmit vertically and provide dynamic suspension/patella-femoral joint lift proportional to the VRB 100 selected resistance to bending.

The VRB resistance and therefore the patella-femoral vertical lift provided by arm 1325 to the knee joint is a function of the selected locked rotated position of the VRB 100.

As previously discussed, as spline 1920 is pulled out of socket 1930, rotated and reinserted into socket 1930, the orientation of VRB 100 is altered from a minimum degree of rigidity to a maximum degree of rigidity. Thus, allowing different levels of rigidity to be imparted to compression assembly 1320.

Although the instant application has been described with regard to a knee brace, it would be appreciated that the assembly may be suitable for other joints. For example, the assembly may be incorporated into a brace suitable for use with an ankle, a wrist or an elbow.

In addition, it would be appreciated that the brace assembly described herein may be incorporated into a full body exoskeleton structure that allows for greater carrying capability as load is maintained through the exoskeleton.

FIG. 20A illustrates a front perspective view of a body exoskeleton in accordance with the principles of the invention.

The exoskeleton, shown in FIG. 20A, delivers mission adaptable, reactive lower extremity/body brace support to protect the foot, ankle, knee and back, by maintaining bio-mechanic weight balance (i.e. dynamic suspension), optimizing body weight load distribution, and efficiently unloading pack weight, to minimize injury, maximize locomotion efficiency for field deployment.

As discussed, variable resistance technology applied to the joints of the body via interconnected or laddered orthotics (i.e. exoskeleton), correct bio-mechanical joint imbalances of the body under heavy loads for the foot, ankle, knee, back and the neck and thus enhance locomotion through running economy with comfort.

The exoskeleton support system 2000 shown in FIG. 20A implements VRBs to act as adjustable resistance cantilevers to provide a selectable range of dynamic and reactive suspension to each joint, centering and correcting bio-mechanical joint imbalances of the body's joints (i.e., foot, ankle, back, knee) of the lower extremities under load, resulting in dynamic bio-mechanical support for bone, connective and musculature structures.

As shown, each foot, ankle, knee brace and back orthotic of the exoskeleton acts individually and in concert to dynamically and reactively support the body. The individual orthotics are connected by height adjustable energy return and or shock absorbing piston rods that further dissipate and cushion load from the body.

As shown in FIG. 20A, the foot orthosis 2010 is connected via a flexible hinge 2015 to ankle orthosis (AFO) 2020 that is connected to the unloading knee brace 2040 via a height adjustable energy return shock absorbing rod or piston 2045 connected to the lower calf armature of the knee brace 2040. Knee brace 2040 has been described with regard to FIG. 13A, for example, and the reader is directed to the description of FIG. 13A for further detail regarding adjustment of the knee brace 2040 using VRB technology.

The top armature 2050 of the knee brace 2040 is connected to the lumbar armature 2060 (i.e., a hip shelf for a rucksack) via height adjustable energy return shock absorbing rod or piston 2065.

Specifically, the unloading knee brace 2040 supports and unloads the patella-femoral knee joint in proportion to the loads placed upon the knee from the downward body and rucksack loads transmitted upon it from the rods or pistons that are connected to the lumbar armature shelf. The exoskeleton and its componentry, shown in FIG. 20A, act as a structural cage around the body to dynamically offload and support weight to assist human movement by maintaining bio-mechanic alignment.

The totality of the interconnected combined components provide an adjustable, dynamic, reactive and supportive exoskeleton structure 2000 to protect the body from load and injury.

Additionally, potentiometer or linear joint (pressure or load) sensors relay information of degree and rate of joint bend to an onboard microcomputer. The enhanced biophysical sensor data provides intelligence to the physical health of the body and pro-active recommendations to prevent or mitigate injury.

In a powered exoskeleton, the enhanced biophysical sensor data augments, controls and amplifies wearer articulation response to move the hydraulic system in real time with the body. The resulting natural movement flow of the system allows persons to more intuitively run, walk, kneel, crawl, and squat.

FIG. 20B illustrates a rear perspective view of a body exo skeleton in accordance with the principles of the invention.
Methods of Sensing and Relaying Biomechanical Performance Data from VRB Deflection In accordance with the principles of the invention, a method or physical, e.g., mechanical sensor or tensor, means of detecting and quantifying biomechanics performance data from VRB deflection in the brace assembly shown in FIGS. 13A and/or 20A may be incorporated in order to monitor in real time the health condition of individual joint operation and movement for stress, strain and loading cycles to prescriptively and pro-actively notify a wearer of potential injury.

In accordance with the principles of the invention, VRB deflection may be determined through the monitoring of the flexing shape of a VRB (Variable Resistance Beam) 100 or multiple VRBs as loads are dynamically applied, quantified and recorded with the wearer notified of loading conditions that would exceed the joints physical ability sustain normal operation without damage, e.g. repetitive strain A few examples of physical sensors to measure and quantify joint stress, strain loading cycles are a Wheatstone bridges, potentiometers, temperature-pressure gauge, foils, piezo resistors, semiconductors, nano-particulates, conductive electroplating, diffraction grating, optical fiber, optical grid (Non-Intrusive Stress Measurement System—NSMS), wire, micro tubes, miniature Wi-Fi transmitters, accelerometers and or other means to detect VRB flexure or movement of any kind.

Physical sensing occurs when VRB 100, or multiple VRBs, is deflected or flexed. As the physical shape of VRB 100 is deformed, an electrical resistance is changed and/or other measurement quality or physical parameter, e.g. optical, physical location or acceleration may be detected.

For example, the Wheatstone bridge determines a difference measurement, which can be extremely accurate. Variations on the Wheatstone bridge can be used to measure capacitance, inductance, impedance and other quantities.

Placement and locations of the biomechanical sensors are typically bonded onto or along the surface length of a VRB, into a side channel and or internally through an interior diameter hole, bore and or extruded geometry to accept and hold the sensor.

In another aspect of the invention, a strain gauge may be incorporated into the knee brace shown in FIG. 13A or in the exoskeleton structure shown in FIG. 20A, wherein advantage is taken of the physical property of electrical conductance and its dependence on the conductor's geometry. For example, when an electrical conductor is stretched within the limits of its elasticity without permanent deformation, the sensor will become narrower and longer. This changes or increases the electrical resistance along the sensors length or end to end.

When measuring electrical resistance of a strain gauge bonded to a VRB, the amount of applied stress may be inferred. As an example, another typical strain gauge arranges a long, thin conductive strip in a zig-zag pattern of parallel lines such that a small amount of stress in the direction of the orientation of the parallel lines results in a multiplicatively larger strain measurement over the effective length of the conductor surfaces in the array of conductive lines—and, hence, a multiplicatively larger change in resistance—than would be observed with a single straight-line conductive wire.

In addition, other methods of sensing VRB deflection, range from temperature (kinetic heating), piezo (milli-volt generation), optical sensing (diffraction grating), to miniature Wi-Fi signaling physical location and or accelerometer chips.

In one aspect of the invention, all sensors are directly wired or connected to a physical circuit or by means of a wireless signal to an embedded printed circuit board (PCB) with processing algorithm, battery and transmitter. The on-board algorithm sends real time biomechanical data to a handheld, worn or remote receiver to alert the wearer to potential injury or current physical condition.

As previously described, resistance ranges are generated by rotating the beams over a fulcrum positioned adjacent to a body joint.

Dynamic support is also beneficial for the recuperative period following operation, rehabilitation, arthritis or during extreme sports. Additionally, resistance beam assemblies may also contribute to shock absorption via a bushing and piston arm mechanically connected to the beam assembly. Furthermore, beam assemblies positioned on each side of a joint act as lateral stabilizers.

In one aspect of the invention, the VRB's 100 may be composed of thermoplastic polymers, especially high tenacity polymers, include the polyamide resins such as nylon; polyolefin, such as polyethylene, polypropylene, as well as their copolymers such as ethylene-propylene; polyesters, such as polyethylene terephthalate and the like; vinyl chloride polymers and the like, and polycarbonate resins, and other engineering thermoplastics such as ABS class or any composites using these resins or polymers. The thermoset resins include acrylic polymers, resole resins, epoxy polymers, and the like.

Polymeric materials may contain reinforcements that enhance the stiffness or flexure of the flexure resistance spine. Some reinforcements include fibers, such as fiberglass, metal, polymeric fibers, graphite fibers, carbon fibers, boron fibers and Nano-composite additives, e.g. carbon nano-tubes, et al, to fill the molecular gaps, therefore strengthening the material.

Additional materials that the resistance rods or VRB's may also be composed of include high tensile aircraft aluminum and high carbon spring steel and/or high tensile strength to weight materials.

Although the different applications of the VRBs shown herein refer to VRB 100 (type I), it would be recognized that each of the applications may incorporate one or more of the other type of VRBs (i.e., type II through type VII) without altering the scope of the invention.

The resilient VRB's shown herein may be used with or in conjunction with sports equipment and exercise apparatus to create meaningful exercise and or other useful mechanisms. For example, devices suitable for exercise equipment, sports equipment, home improvement and medical mobility may be created to selectable control bending strength or resistance ranges to impart performance benefits. VRB's may be secured at one or more fixed points with the appropriate device may be used to provide appropriate variable resistance. In addition, the VRBs may be handheld at various points along the beam length to affect fulcrum resistance and or rotated to different incremental orientations to affect resistance with discrete geometric cross sections. In one aspect of the invention, VRB's may be perpendicularly mounted to a variety of mechanical apparatus to affect resistance and may additionally be handheld in the air to expand the exercise envelop.

The VRB's described herein may be manufactured based on a method selected from a group consisting of: rapid prototyping, stereolithography, molding, casting, extrusion and other known forms in the art.

VRB's, which may be solid, semi-hollow or hollow, with or without geometrically created I-beam effect (i.e., spines) on the outside or interior diameter generates resistance depending on the axis of orientation and/or a fulcrum position has been described herein. VRB's 100, with incorporated I-beam geometry on the outside diameter, can allow for the dynamic adjustment of resistance of the device. An advantage of a device including a VRB's described herein may be-compact, lightweight and offer the ability to more easily and quickly change a desired level of resistance than is typically found in units using weights, rubber bands, bows or springs. By simple hand reposition, as shown in FIG. 15B, or rotation of beam of the incorporated into the device a desired resistance level may be achieved. The VRB's 100 disclosed, herein, can provide resistance, depending on the orientation of the beam, to the user. In addition, the device can vary the resistance provided to the user during an exercise, without interrupting the exercise cycle. Additional beam resistance is achieved depending upon the relative orientation of the beam within a 180° degree hemisphere of movement relative to the user. Hence, according to the principles of the invention, a progressive dynamic resistance may be achieved with a variation of the orientation of the beam or shaft shown herein.

The principle of Progressive Dynamic Resistance (PDR) are:
controlled and rotatable (variable) resistance beam with ergonomic work zones:

Multiple, sequential, mechanical resistances are achieved for the purpose of rehabilitation and exercising of endo-skeletal musculature.

Increased/decreased incremental mechanical resistance and exercise adjustability is achieved through beam rotation and or fulcrum hand position relative to the beam or arc length/distance along the resistance beam to impart desired work load.

PDR's 180° or 360° degree range of dynamic arcing motion provides an exercise resistance program for every male or female body type with variability in muscle size and strength to provide gain after unilateral resistance training of progressive resistance exercise (PRE).

PDR's incremental mechanical resistance capability (i.e., resistance adjustability through rotation and or fulcrum hand position) facilitates and customizes the user's strength curve and exercise requirements from simply moving hand/leg position to tailor the optimum resistance to maximize the workout of the targeted muscle group.

PDR resistance beam technology does not have mechanical flat spots or dead spots and provides continuous resistance curve to maximize workout loading on the targeted muscle groups, thus creating a more effective work out.

PDR's bend/arc/range of motion means that as the resistance beam is bent farther away from a plane of minimum resistance, the sustained mechanical resistance incrementally increases, creating a progressively more intense and effective work out/work load on the target muscle group.

Continuous Progressive Dynamic Resistance loading from the bending of VRB's 100 is a highly effective bio-mechanical exercise.

Figure 3:
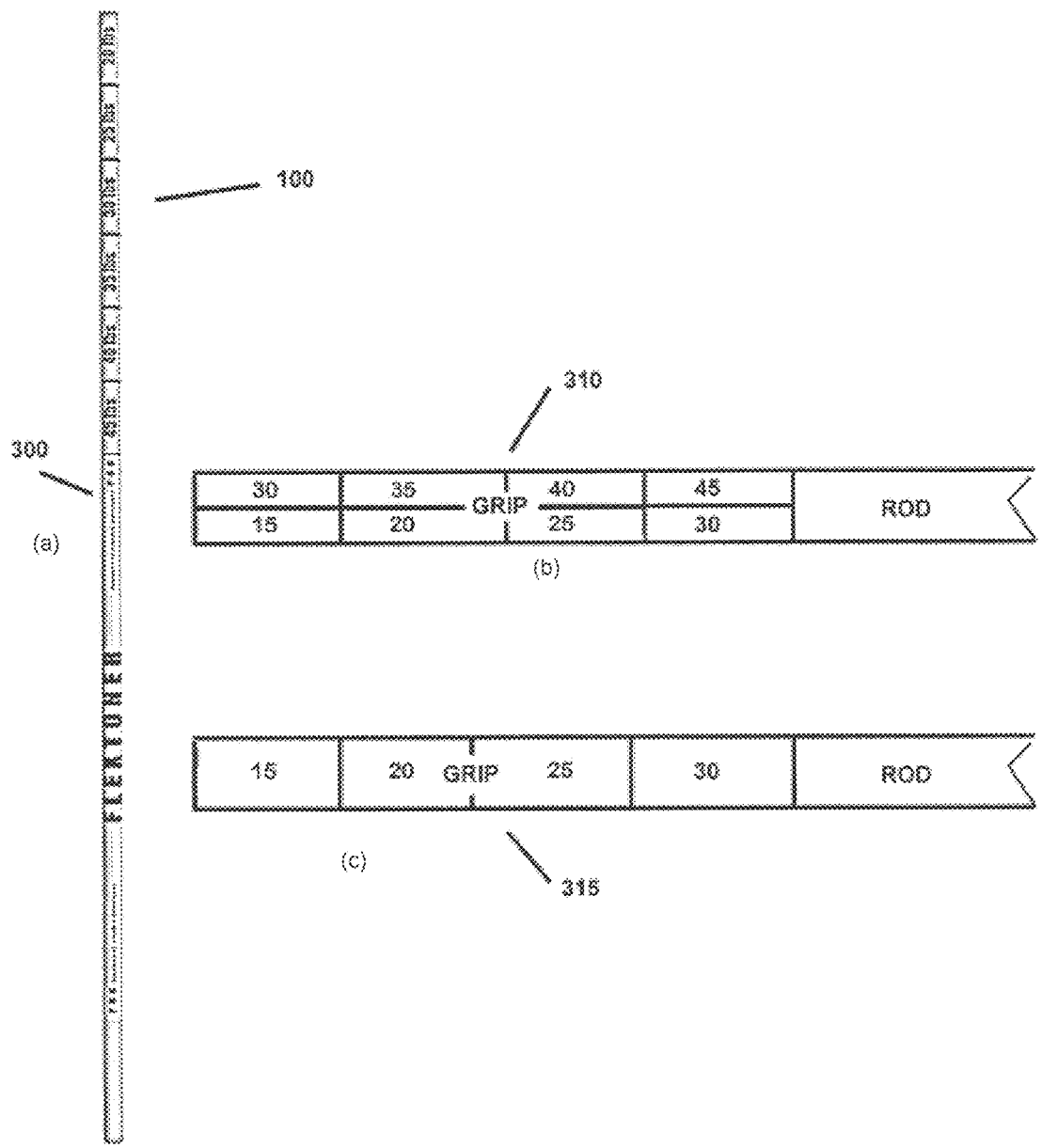
FIG. 3(a)-FIG. 3(c) illustrates a rod with an outside diameter with marked sets of indicia that specify the range of flexural resistances proportionate to the tensile strength of the beam material and fulcrum length per hand position[s]

In other aspects of the invention, different types of sport equipment and apparatus may incorporate the VRB's 100 technology described herein. Examples in which VRB 100 technology may be applied are:

FlexGym & FlexTrax products represent an apparatus or structure to hold a plurality of rod holders into which VRB 100 resilient adjustable or non-adjustable solid or tubular rods and other exercise apparatus are inserted to allow users to perform a variety of exercises. FIGS. 3, 4 and 5 illustrate an exemplary system in accordance with the principles of the invention.

FlexBoard product represents an apparatus or structure wherein a transportable structural panel resting on the ground with rod holders into which VRB's 100 are inserted perpendicularly to allow users to perform a variety of exercises. FIG. 6 illustrates an exemplary FlexBoard system in accordance with the principles of the invention.

FlexGym represents an apparatus or structure wherein the VRB 100 technology of the present invention may be incorporated into a plurality of structural tracks with rod holders providing multiple positions into which the VRB 100 resilient adjustable or non-adjustable solid or tubular rods and other exercise apparatus are inserted to allow users to perform a variety of exercises in an I-formed structure, with a cantilevered bench that folds down or may be a free form bench. In addition, the floor tracks, which also comprise the lower structure of the unit, can be optionally retracted to the vertical tracks when not in use.

In one aspect of the invention a means to track and record exercise cycles per set of the user may be incorporated. For example, biometric data of the user may be recorded on a smart card, a smart phone, a computer, etc. so exercise cycles can be recorded. In addition, biometric data of the user may be conveyed by magnet, reflector, RFID, Wi-Fi or other means to measure or quantify exercise cycle.

In another aspect of the invention, the exercise apparatus may include sensors (e.g., Wi-Fi) to sense proximity of the user as the user approaches the exercise apparatus. The sensors may also be in communication with a user's smart phone transmitter or other technical means and the exercise apparatus respond may be setup to correspond to a user's particular exercise regime.

Another embodiment of the exercise apparatus sensors would recognize a user via sensor or Wi-Fi or iPhone transmitter that would initiate servo-mechanisms to proactively set a customized workout cycle. This would mean that the track holder along the track, be it vertical or horizontal, and would be matched to the user's ergonomic body size and requirements.

In another aspect of the invention a video display or monitor may be incorporated to enable a user to receive instructions regarding a particular exercise or to watch one or more programs of interest during the exercise session.

Returning to FIG. 3, FIG. 3 represents a method for incorporating the VRB 100 technology into an apparatus for exercise with one or more anchor point which is represented by the product FlexToner. More specifically, the present invention related to a resilient adjustable or non-adjustable solid or tubular rod exercise apparatus handheld at one or more places and flexed.

Other VRB 100 exercise apparatus applications are, but not limited to, upper and or lower body exercise machines: (e.g. treadmills, stair climbers, elliptical trainers, stationary bikes, mobility, medical, rehabilitative systems that create and control selectable bending strength or resistance ranges with fixed rotation to impart PDR) isolating the upper and or lower body for exercise.

The present invention may be incorporated into devices that provide for low impact/low resistance exercises (e.g., Rehabilitative and Geriatric exercisers) to strengthen and rehabilitate post surgical, bed-ridden, sport injury and or geriatric benefit. Typically, these devices may employ VRBs 100 that are matched to the strength of the user. For example, VRB 100 may be adjusted to provide rigid support during an initial healing phase of a sports injury and then adjusted to provide lesser amount of support to compensate for progress during the healing of the sport injury.

Although, the present invention is described with regard to a plurality of different equipment, it would be recognized that the described equipment are merely examples to which the VRB technology described herein may be applied. The examples provided herein are merely illustrative of the application of the claimed technology and the examples are not intended to limit the subject matter claimed.

In other aspects of the invention, other types of sports equipment and apparatus may incorporate the VRB 100 technology described herein. Examples in which VRB 100 technology may be applied are, but not limited to:

Golf Clubs

Golf clubs may be formed of graphite, wood, titanium, glass fiber or various types of composites or metal alloys. Each varies to some degree with respect to stiffness and flexibility. However, golfers generally carry onto the golf course only a predetermined number of golf clubs.

Varying the stiffness or flexibility of the golf club is not possible, unless the golfer brings another set of clubs of a different construction. Even in that case, however, the selection is still somewhat limited.

Nevertheless, it is impractical to carry a huge number of golf clubs onto the course, each club having a slight nuance of difference in flexibility and stiffness than another. Golf players prefer taking onto the course a set of clubs that are suited to the player's specific swing type, strength and ability.

Returning to FIG. 8, which illustrates an exemplary embodiment of an internal VRB 100 in a hollow shaft (e.g., a golf shaft). As previously discussed, the VRB 100 is centrally raised or lowered within the golf shaft, the fulcrum or kick point is raised or lowered, thereby changing the shaft flex. The 360 degree symmetrical geometry provides a solution for an adjustable golf club and would be fully compliant with the existing USGA rules of golf and assorted international golf associations.

Running Shoes, Training Shoes, Basketball Shoes

The transmission of the shoe wearer's strength (power) from their legs into the ground is directly affected by the sole stiffness of the shoe. Runners may gain more leverage and, thus more speed, by using a stiffer sole. Basketball players may also affect the height of their jumps through the leverage transmitted by the sole of their shoes. If the sole is too stiff, however, the toe-heel flex of the foot is hindered.

It is advantageous that the shoe wearer have the ability to tailor the sole stiffness to his/her individual weight, strength, height, running style, and ground conditions. Preferably, the shoe wearer may tailor the stiffness of the shoe sole to affect the degree of power and leverage that is to be transmitted from the wearer into the ground.

In this example, VRB 100 are insertable, insert molded or structurally connected to the shoe sole in lateral and/or longitudinal positions within the sole and are all rotatable to a fixed and mechanically locked position to effect custom flexural resistance range. Additionally, zones of resistance are customizable, e.g. the right pad of the foot can be made more rigid than the left pad side through the beam's rotated orientation. Thus, the degree of flexibility may be customized to accommodate a user's desired preferences.

Incorporation of the VRB 100 technology into running shoes, as shown in FIG. 11, provides a dynamic adjustable in-sole suspension system that can absorb the weight of the wearer and release it per each step.

Hockey Sticks

Hockey includes, but is not limited to, ice hockey, street hockey, roller hockey, field hockey and floor hockey.

Hockey players may require that the flexure of the hockey stick be changed to better assist in the wrist shot or slap shot needed at that particular junction of a game or which the player was better at making. Players may not usually leave the field to switch to a different piece of equipment during play.

Younger players may require more flex in the hockey stick due to lack of strength and such flex may mean the difference between the younger player being able to lift the puck or not when making a shot since a stiffer flex in the stick may not allow the player to achieve such lift.

In addition, as the younger players ages and increases in strength, the player may desire a stiffer hockey stick, which in accordance with convention means the hockey player would need to purchase additional hockey stick shafts with the desired stiffness and flexibility characteristics. Indeed, to cover a full range of nuances of differing stiffness and flexibility characteristics, hockey players would have available many different types of hockey sticks.

Even so, the hockey player may merely want to make a slight adjustment to the stiffness or flexibility of a given hockey stick to improve the nuances of the play. Thus, the incorporation of the VRB technology into hockey sticks (shaft and/or blade) provides for variations in the stiffness and flexibility that may be adjusted as the user progresses in their ability.

Incorporation of the VRB technology into hockey sticks is similar to that shown in FIG. 7.

In other aspects of the invention, different type of Do-it-Yourself (DIY) and Home Improvement products and devices may incorporate the VRB technology described herein. Examples in which VRB technology may be applied are:

Lawn Equipment:

Adjustable lawn rake with VRB 100 tines:

The VRB 100 technology described by the present invention may be incorporated into a lawn rake. In this case, an adjustable rake with a rotatable VRB 100 down the shaft of the rake may be created. The VRB 100 facilitates the adjustment of the lawn rake, with the ability to adjust stiffness of the shaft relative to the load (e.g., light grass clippings, heavy grass clipping, wet grass clippings).

Incorporation of the VRB 100 technology into lawn rake (or other similar handled devices) is similar to that shown in FIG. 10A and FIG. 10B.

In another embodiment, the VRB 100 technology described by the present invention may be incorporated into tines of a lawn rake creating an adjustable rake. Thus, the VRB 100 facilitates the adjustment of a lawn/utility rake by providing the ability to create variable shaft resistance for light or heavy duty gravel raking due to its rotated orientation. The VRB 100 adjustment setting may simultaneously rotate the rake's tines from 0° to 90°, thus affecting a stiffer tine orientation. The tines may be elliptical or oval in shape in an embodiment of an elliptical VRB 100. When the tines are in a 0° orientation, they are the most flexible and suitable for raking leaves or light duty yard work. When the tines are in a 90° orientation, they are the most rigid and suitable for raking heavy duty gravel. The flexural change of tines can be further impacted by means of adjusting where the center point of a fulcrum of the flex of tines is located.

FIG. 10A illustrates an exemplary lawn rake incorporating the VRB 100 technology disclosed herein. FIG. 10A and FIG. 10B illustrates a rake assembly 1000 including a handle 1010 and a tine assembly 1015 including a plurality of VRB 100 tines that are simultaneously adjusted through rotation. FIG. 10B illustrates a bottom view of rake 1000 showing the orientation of the tines 100 at a maximum resistance level (90 degree orientation).

Thus, the incorporation of the VRB 100 technology in the tines creates a flexible lawn rake to alter the flex characteristics of the rake.

Although, the present invention is described with regard to a plurality of different lawn equipment, it would be recognized that the lawn equipment described herein are merely examples to which the VRB technology described herein may be applied. The examples provided herein are merely illustrative of the application of the claimed technology and the examples are not intended to limit the subject matter claimed.

In other aspects of the invention, different type of medical products and devices may incorporate the VRB technology described herein. Additional examples in which VRB technology may be applied are: Mobility assistance and Rehabilitative Braces that provide dynamic support and suspension for joints and orthotic braces: Foot, ankle, knee, hip, back, shoulder, elbow, wrist, neck (i.e., Prophylactic, Functional Support, Post-operative, Unloader and or Extreme Sports, acting as a second compression driven reactive joint, et al.).

In this aspect of the invention, the VRBs 100 may be used to create a medical brace or orthotic device that by provides a dynamic support and suspension system with variable and adjustable resistance settings to achieve an adjustable performance range so as to customize the brace or device during the recuperation stage of the wearer, acting as external supporting spring ligament or adjustable box spring structure and/or further supported by a conformal brace framework. For example, the conformal brace framework may be a mechanical joint and/or a flexible webbing, e.g., Ballistic nylon/Neoprene et al.

In one aspect of the invention, the medical brace or orthotic device may be used to:

1. control, guide, limit and/or immobilize an extremity, joint or body segment for a particular reason;
2. To restrict movement in a given direction;
3. To assist movement generally;
4. To reduce weight bearing forces for a particular purpose;
5. To aid rehabilitation from fractures after the removal of a cast; and
6. To otherwise correct the shape and/or function of the body, to provide easier movement capability or reduce pain.

Although, the present invention is described with regard to knee brace, FIG. 12, it would be recognized that the described braces are merely examples to which the VRB technology described herein may be applied. The examples provided herein are merely illustrative of the application of the claimed technology and the examples are not intended to limit the subject matter claimed. For example, the VRB technology described herein may be applied to braces that are used for the back, arm, elbow, neck, and legs, without altering the scope of the invention.

In another aspect of the VRB technology described herein, braces or devices may be constructed wherein the VRB beams are equipped with attached sensors [e.g. Electrogoniometer] to provide continuous bio-mechanic feedback or other biomechanical sensor means of medical or injury diagnostic. For example, compression, extension, articulation, range and/or twisting measurements may be made and provided to a network (e.g., a WIFI, wireless) to monitor the movement of the user.

In another aspect of the invention, the braces including the VRB technology described herein may include sensors, such as impedance wire sensors, accelerometer, stressors, etc., to measure flexural strength, cycle counts per day to measure Joint performance, injury, damage assessment, etc., so that an appropriate monitoring of the healing of the effected joint may be monitored. Such monitoring is valuable in the field of professional sports medicine, for example.

In still another embodiment of the VRB technology described herein provides further benefits in the medical profession, wherein a VRB may be made from a BIO-Degradable Polymer that may be incorporated into an Internal Fixation brace. In this case, the internal VRB may be rotatable using outside setting pins connected to an internal worm gear at the head of the internal VRB. The main benefit of bio-degradable VRB fixation beams is that they require no post-operative surgery to remove. The biopolymers may be of a non-toxic material capable of maintaining strong mechanical integrity until engineered to degrade, wherein controlled rates of degradation (typically a function of crystallinity) are predetermined. An additional benefit is to not create an immune response and or the products of degradation must also be non-toxic.

Controlled degradation rates may be affected by a percentage of polymer crystallinity, molecular weight, hydrophobicity and location within the body.

Examples of promising biodegradable polymers to be made into VRBs through extrusion and or injection molding are, but not limited to, 3-hydroxypropionic acid, the suture polymer Polyglycolide and or Poly(lactic acid) or polylactide (PLA). A thermoplastic aliphatic polyester that degrades into lactic acid, a natural waste product of the body.

Although the different applications of the VRB shown herein refer to VRB 100 (type I), it would be recognized that each of the applications may incorporate one or more of the other type of VRBs (i.e., type II through type VII) without altering the scope of the invention.

The specification is to be regarded in an illustrative manner, rather than with a restrictive view, and all such modifications are intended to be included within the scope of the invention.

Benefits, advantages, and solutions to problems have been described above with regard to specific embodiments. The benefits, advantages, and solutions to problems, and any element(s) that may cause any benefits, advantages, or solutions to occur or become more pronounced, are not to be construed as a critical, required, or an essential feature or element of any or all of the claims.

While there has been shown, described, and pointed out fundamental novel features of the present invention as applied to preferred embodiments thereof, it will be understood that various omissions and substitutions and changes in the apparatus described, in the form and details of the devices disclosed, and in their operation, may be made by those skilled in the art without departing from the spirit of the present invention. It is expressly intended that all combinations of those elements that perform substantially the same function in substantially the same way to achieve the same results are within the scope of the invention. Substitutions of elements from one described embodiment to another are also fully intended and contemplated. For example, any numerical values presented herein are considered only exemplary and are presented to provide examples of the subject matter claimed as the invention. Hence, the invention, as recited in the appended claims, is not limited by the numerical examples provided herein.

What is claimed is:

1. An exoskeleton brace for supporting a joint, said brace comprising:
    an upper brace assembly;
    a lower brace assembly; and
    a hinge positioned between the upper brace assembly and the lower brace assembly, said hinge allowing rotation of the upper brace assembly about a focal point with respect to said lower brace assembly;
    an adjustable assembly configured to apply a variable force to the focal point, the adjustable assembly comprising:
        a piston slidable within the adjustable assembly, said piston configured to contact the focal point;
        a bushing; and
        a variable resistance beam positioned transverse to the adjustable assembly between the piston and the bushing, wherein said variable resistance beam is cantilevered with respect to the bushing, wherein a cross-sectional view of said variable resistance bean comprises at least one of: rectangular, elliptical, sculptured, internal spine, and external spine; and a gear assembly configured to rotate the variable resistance beam from a first position to a second position, said first position corresponding to a position wherein a minimum axis of said variable resistance beam contacts said bushing and said second position corresponding to a position wherein a major axis of said variable resistance beam contacts said bushing.

2. The exoskeleton brace as claimed in claim 1, wherein said variable resistance beam is composed of a material selected from a group consisting of: plastics, thermoplastic polymers, copolymers, polyesters, vinyl chloride polymers and polycarbonate resin, metals, and re-enforced plastics.

3. The exoskeleton brace as claimed in claim 1, wherein said bushing comprises:
   an elastomer material.

4. The exoskeleton brace as claimed in claim 1, wherein said bushing comprises:
   an upper surface; and
   a lower surface, said upper surface contacting said variable resistance beam.

5. The exoskeleton brace as claimed in claim 1, wherein said upper surface of said bushing is selected from a group consisting of:
   a flat shape and a convex shape.

6. The exoskeleton brace as claimed in claim 1, further comprising:
   an indicia, said indicia representative of said variable resistance beam rotation.

7. The exoskeleton brace as claimed in claim 1, further comprising:
   an upper attachment strap incorporated into the upper brace assembly; and
   a lower attachment strap incorporated into the lower brace assembly.

8. A knee brace supporting a knee comprising:
   a thigh attachment member including an upper extension positioned above said knee;
   a calf attachment member including a lower extension positioned below said knee;
   a hinge positioned between said upper extension on a first end and said lower extension on a second end,
   a compression assembly incorporated into one of said upper extension and said lower extension, said compression assembly comprising:
      a housing containing therein:
         a piston, slidable within said housing, attached to said hinge,
         a bushing opposite said piston; and
         a variable resistance beam positioned cantilevered with respect to the bushing, said variable resistance beam positioned at an angle offset from a horizontal plane above the bushing, said variable resistance beam comprising:
            a major axis and a minor axis substantially perpendicular to the major axis, wherein a cross-sectional view of said variable resistance beam comprises one: rectangular, elliptical, sculptured, internal spine, and external spine; and
      a gear assembly engaging a geared head of said variable resistance beam, said gear assembly configured to orient one of the major axis and the minor axis to contact the piston.

9. The knee brace as claimed in claim 8, wherein said bushing comprises:
   a concave upper surface contacting said variable resistance beam.

10. The knee brace as claimed in claim 8, wherein said variable resistance beam is composed of a material selected from a group consisting of: plastics, thermoplastic polymers, copolymers, polyesters, vinyl chloride polymers and polycarbonate resin, metals, re-enforced plastics and nano-reinforced plastics.

11. The knee brace as claimed in claim 8, wherein said bushing is composed of an elastomer material.

* * * * *